United States Patent
Graetzel et al.

(10) Patent No.: US 11,666,393 B2
(45) Date of Patent: Jun. 6, 2023

(54) SYSTEMS AND METHODS FOR MEDICAL INSTRUMENT COMPRESSION COMPENSATION

(71) Applicant: Auris Health, Inc., Redwood City, CA (US)

(72) Inventors: Chauncey F. Graetzel, Palo Alto, CA (US); June Gyu Park, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/586,631

(22) Filed: Sep. 27, 2019

(65) Prior Publication Data
US 2020/0038123 A1 Feb. 6, 2020

Related U.S. Application Data

(62) Division of application No. 15/640,277, filed on Jun. 30, 2017, now Pat. No. 10,426,559.

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 34/10* (2016.02);
(Continued)

(58) Field of Classification Search
CPC ............ A61B 1/00147; A61B 1/00149; A61B 2034/301; A61B 34/30
See application file for complete search history.

(56) References Cited

U.S. PATENT DOCUMENTS 4,644,237 A   2/1987   Frushour et al.
4,745,908 A   5/1988   Wardle
(Continued)

FOREIGN PATENT DOCUMENTS

CN   1364275   8/2002
CN   1511249   7/2004
(Continued)

OTHER PUBLICATIONS

Kukuk, Oct. 5, 2001, TBNA—protocols: Guiding TransBronchial Needle Aspirations Without a Computer in the Operating Room, MICCAI 2001, 2208:997-1006.
(Continued)

*Primary Examiner* — John P Leubecker
(74) *Attorney, Agent, or Firm* — Chang & Hale LLP

(57) ABSTRACT

Certain aspects relate to systems and techniques for compensating for compression in elongated shafts of medical instruments. Medical instruments can include elongated shafts that may experience compression when articulated. The medical instruments can be attached to instrument positioning devices that are configured to move the medical instruments to compensate for this compression. For example, an instrument positioning device can advance a medical instrument to compensate for compression in an elongated shaft of the medical instrument. In some instances, the amount of compression is determined using a compression compensation parameter. The compression compensation parameter can be determined during a calibration process of the medical instrument.

27 Claims, 22 Drawing Sheets

(51) Int. Cl.
*A61B 90/00* (2016.01)
*A61B 34/00* (2016.01)
*A61B 90/98* (2016.01)
*A61B 34/10* (2016.01)
*A61B 34/20* (2016.01)
*A61B 1/00* (2006.01)

(52) U.S. Cl.
CPC ............ *A61B 34/20* (2016.02); *A61B 34/25* (2016.02); *A61B 34/71* (2016.02); *A61B 90/98* (2016.02); *A61B 1/00149* (2013.01); *A61B 2017/00323* (2013.01); *A61B 2017/00327* (2013.01); *A61B 2017/00477* (2013.01); *A61B 2034/2051* (2016.02); *A61B 2034/2061* (2016.02); *A61B 2034/301* (2016.02); *A61B 2034/715* (2016.02); *A61B 2090/064* (2016.02); *A61B 2090/067* (2016.02); *A61B 2217/005* (2013.01); *A61B 2217/007* (2013.01)

(56) References Cited

U.S. PATENT DOCUMENTS

| | | |
|---|---|---|
| 4,748,969 A | 6/1988 | Wardle |
| 5,194,791 A | 3/1993 | Cull |
| 5,251,611 A | 10/1993 | Zehel |
| 5,280,781 A | 1/1994 | Oku |
| 5,408,263 A | 4/1995 | Kikuchi |
| 5,672,877 A | 9/1997 | Liebig et al. |
| 5,769,086 A | 6/1998 | Ritchart |
| 5,899,851 A | 5/1999 | Koninckx |
| 6,004,016 A | 12/1999 | Spector |
| 6,198,974 B1 | 3/2001 | Webster, Jr. |
| 6,246,200 B1 | 6/2001 | Blumenkranz et al. |
| 6,459,926 B1 | 10/2002 | Nowlin |
| 6,690,963 B2 | 2/2004 | Ben-Haim |
| 6,837,846 B2 | 1/2005 | Jaffe |
| 7,197,354 B2 | 3/2007 | Sobe |
| 7,607,440 B2 | 10/2009 | Coste-Maniere et al. |
| 7,763,015 B2 | 7/2010 | Cooper et al. |
| 7,772,541 B2 | 8/2010 | Froggatt et al. |
| 7,963,288 B2 | 6/2011 | Rosenberg et al. |
| 8,335,557 B2 | 12/2012 | Maschke |
| 8,348,931 B2 | 1/2013 | Cooper et al. |
| 8,376,934 B2 | 2/2013 | Takahashi |
| 8,396,595 B2 | 3/2013 | Dariush |
| 8,442,618 B2 | 5/2013 | Strommer et al. |
| 8,469,945 B2 | 6/2013 | Schena |
| 8,498,691 B2 | 7/2013 | Moll et al. |
| 8,506,555 B2 | 8/2013 | Ruiz Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,894,610 B2 | 11/2014 | MacNamara et al. |
| 8,929,631 B2 | 1/2015 | Pfister et al. |
| 8,945,095 B2 | 2/2015 | Biumenkranz |
| 9,014,851 B2 | 4/2015 | Wong et al. |
| 9,023,060 B2 | 5/2015 | Cooper et al. |
| 9,057,600 B2 | 6/2015 | Walker et al. |
| 9,129,417 B2 | 9/2015 | Zheng et al. |
| 9,173,713 B2 | 11/2015 | Hart et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,283,046 B2 | 3/2016 | Walker et al. |
| 9,289,578 B2 | 3/2016 | Walker et al. |
| 9,302,702 B1 | 4/2016 | Schepmann |
| 9,314,306 B2 | 4/2016 | Yu |
| 9,345,456 B2 | 5/2016 | Tsonton et al. |
| 9,358,682 B2 | 6/2016 | Ruiz Morales |
| 9,452,276 B2 | 9/2016 | Duindam et al. |
| 9,498,291 B2 | 11/2016 | Balaji et al. |
| 9,504,604 B2 | 11/2016 | Alvarez |
| 9,522,034 B2 | 12/2016 | Johnson |
| 9,532,840 B2 | 1/2017 | Wong et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,810 B2 | 10/2017 | Schuh |
| 9,789,608 B2 | 10/2017 | Itkowitz et al. |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wailace et al. |
| 9,931,025 B1 | 4/2018 | Graetzei et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,843 B2 | 11/2018 | Wong et al. |
| 10,130,345 B2 | 11/2018 | Wong et al. |
| 10,136,959 B2 | 11/2018 | Mintz et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,206,746 B2 | 2/2019 | Walker et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,321,900 B2 | 6/2019 | Au et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,583,271 B2 | 3/2020 | Bogusky |
| 10,753,439 B2 | 8/2020 | Awtar |
| 10,765,487 B2 | 9/2020 | Ho |
| 2001/0000040 A1 | 3/2001 | Adams et al. |
| 2001/0021843 A1 | 9/2001 | Bosselmann et al. |
| 2002/0035330 A1 | 3/2002 | Cline |
| 2002/0077533 A1 | 6/2002 | Bieger et al. |
| 2002/0161280 A1 | 10/2002 | Chatenever et al. |
| 2002/0173878 A1 | 11/2002 | Watanabe |

(56) References Cited

U.S. PATENT DOCUMENTS

| | | |
|---|---|---|
| 2003/0045778 A1 | 3/2003 | Ohline |
| 2003/0181809 A1 | 9/2003 | Hall et al. |
| 2003/0182091 A1 | 9/2003 | Kukuk |
| 2004/0072066 A1 | 4/2004 | Cho et al. |
| 2004/0257021 A1 | 12/2004 | Chang et al. |
| 2005/0043718 A1 | 2/2005 | Madhani |
| 2005/0065400 A1 | 3/2005 | Banik |
| 2005/0107917 A1 | 5/2005 | Smith et al. |
| 2005/0222554 A1 | 10/2005 | Wallace et al. |
| 2005/0234293 A1 | 10/2005 | Yamamoto |
| 2005/0256398 A1 | 11/2005 | Hastings |
| 2005/0261551 A1 | 11/2005 | Couvillon |
| 2005/0272975 A1 | 12/2005 | McWeeney et al. |
| 2006/0015096 A1 | 1/2006 | Hauck et al. |
| 2006/0041293 A1 | 2/2006 | Mehdizadeh |
| 2006/0079745 A1 | 4/2006 | Viswanathan et al. |
| 2006/0200026 A1 | 9/2006 | Wallace et al. |
| 2006/0200049 A1 | 9/2006 | Leo et al. |
| 2006/0258938 A1 | 11/2006 | Hoffman et al. |
| 2007/0013336 A1 | 1/2007 | Nowlin et al. |
| 2007/0043455 A1 | 2/2007 | Viswanathan |
| 2007/0135886 A1 | 6/2007 | Maschke |
| 2007/0142971 A1 | 6/2007 | Schena |
| 2007/0150155 A1 | 6/2007 | Kawai |
| 2007/0249911 A1 | 10/2007 | Simon |
| 2007/0253599 A1 | 11/2007 | White et al. |
| 2007/0287992 A1 | 12/2007 | Diolaiti |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli et al. |
| 2008/0147089 A1 | 6/2008 | Loh |
| 2008/0159653 A1 | 7/2008 | Dunki-Jacobs et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0005768 A1 | 1/2009 | Sharareh |
| 2009/0062813 A1 | 3/2009 | Prisco |
| 2009/0076534 A1 | 3/2009 | Shelton |
| 2009/0184825 A1 | 7/2009 | Anderson |
| 2009/0198298 A1 | 8/2009 | Kaiser et al. |
| 2009/0245600 A1 | 10/2009 | Hoffman |
| 2009/0256905 A1 | 10/2009 | Tashiro |
| 2009/0275940 A1 | 11/2009 | Malackowski et al. |
| 2009/0287354 A1 | 11/2009 | Choi |
| 2009/0324161 A1 | 12/2009 | Prisco |
| 2010/0030061 A1 | 2/2010 | Canfield |
| 2010/0030115 A1 | 2/2010 | Fujimoto |
| 2010/0069920 A1 | 3/2010 | Naylor et al. |
| 2010/0076263 A1 | 3/2010 | Tanaka |
| 2010/0121138 A1 | 5/2010 | Goldenberg et al. |
| 2010/0168918 A1 | 7/2010 | Zhao |
| 2010/0170519 A1* | 7/2010 | Romo ............... A61B 34/30 128/852 |
| 2010/0204713 A1 | 8/2010 | Ruiz |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco |
| 2011/0021926 A1 | 1/2011 | Spencer |
| 2011/0082366 A1 | 4/2011 | Scully et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0218676 A1 | 9/2011 | Okazaki |
| 2011/0257480 A1 | 10/2011 | Takahashi |
| 2011/0258842 A1 | 10/2011 | Dukesherer et al. |
| 2011/0319714 A1 | 12/2011 | Roelle et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0069167 A1 | 3/2012 | Liu et al. |
| 2012/0071752 A1 | 3/2012 | Sewell |
| 2012/0071822 A1 | 3/2012 | Romo et al. |
| 2012/0071894 A1 | 3/2012 | Tanner et al. |
| 2012/0123441 A1 | 5/2012 | Au |
| 2012/0130217 A1 | 5/2012 | Kauphusman et al. |
| 2012/0209293 A1 | 8/2012 | Carlson |
| 2012/0215094 A1 | 8/2012 | Rahimian et al. |
| 2012/0253276 A1 | 10/2012 | Govari et al. |
| 2012/0283745 A1 | 11/2012 | Goldberg et al. |
| 2012/0289777 A1 | 11/2012 | Chopra |
| 2012/0302869 A1 | 11/2012 | Koyrakh |
| 2012/0328077 A1 | 12/2012 | Bouvier |
| 2013/0018306 A1 | 1/2013 | Ludwin |
| 2013/0085330 A1 | 4/2013 | Ramamurthy et al. |
| 2013/0090530 A1* | 4/2013 | Ramamurthy ......... A61B 5/065 600/182 |
| 2013/0102846 A1 | 4/2013 | Sjostrom |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle |
| 2013/0204124 A1 | 8/2013 | Duindam |
| 2013/0218005 A1 | 8/2013 | Desai |
| 2013/0303891 A1 | 11/2013 | Chopra |
| 2013/0303892 A1 | 11/2013 | Zhao |
| 2013/0325030 A1 | 12/2013 | Hourtash et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0235943 A1 | 8/2014 | Paris |
| 2014/0257334 A1 | 9/2014 | Wong et al. |
| 2014/0264081 A1 | 9/2014 | Walker et al. |
| 2014/0275985 A1 | 9/2014 | Walker et al. |
| 2014/0276392 A1 | 9/2014 | Wong et al. |
| 2014/0276394 A1 | 9/2014 | Wong et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0276938 A1 | 9/2014 | Hsu et al. |
| 2014/0277333 A1 | 9/2014 | Lewis et al. |
| 2014/0277747 A1 | 9/2014 | Walker et al. |
| 2014/0296870 A1 | 10/2014 | Stern et al. |
| 2014/0296872 A1* | 10/2014 | Cooper ............... A61M 13/003 606/130 |
| 2014/0309649 A1 | 10/2014 | Alvarez et al. |
| 2014/0316420 A1 | 10/2014 | Ballard et al. |
| 2014/0343416 A1 | 11/2014 | Panescu |
| 2014/0343569 A1 | 11/2014 | Turner |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0073267 A1 | 3/2015 | Brannan |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119638 A1 | 4/2015 | Yu et al. |
| 2015/0150635 A1 | 6/2015 | Kilroy |
| 2015/0164594 A1 | 6/2015 | Romo et al. |
| 2015/0164596 A1 | 6/2015 | Romo et al. |
| 2015/0202015 A1 | 7/2015 | Elhawary |
| 2015/0223902 A1 | 8/2015 | Walker et al. |
| 2015/0255782 A1 | 9/2015 | Kim et al. |
| 2015/0265359 A1* | 9/2015 | Camarillo ......... A61M 25/0147 604/95.04 |
| 2015/0265807 A1 | 9/2015 | Park et al. |
| 2015/0297864 A1 | 10/2015 | Kokish et al. |
| 2015/0305650 A1 | 10/2015 | Hunter |
| 2015/0311838 A1 | 10/2015 | Moule |
| 2015/0314110 A1 | 11/2015 | Park |
| 2015/0335480 A1 | 11/2015 | Alvarez et al. |
| 2015/0342695 A1 | 12/2015 | He |
| 2015/0359597 A1 | 12/2015 | Gombert et al. |

(56) References Cited

U.S. PATENT DOCUMENTS

| | | |
|---|---|---|
| 2015/0374956 A1 | 12/2015 | Bogusky |
| 2015/0375399 A1 | 12/2015 | Chiu et al. |
| 2016/0000414 A1 | 1/2016 | Brown |
| 2016/0000495 A1 | 1/2016 | Elliott |
| 2016/0001038 A1 | 1/2016 | Romo et al. |
| 2016/0005168 A1 | 1/2016 | Merlet |
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0075030 A1 | 3/2016 | Takahashi |
| 2016/0081568 A1 | 3/2016 | Kolberg |
| 2016/0089213 A1 * | 3/2016 | Crews .................. A61B 34/30 606/130 |
| 2016/0100772 A1 | 4/2016 | Ikuma |
| 2016/0128992 A1 | 5/2016 | Hudson |
| 2016/0135908 A1 | 5/2016 | Takahashi et al. |
| 2016/0175059 A1 | 6/2016 | Walker et al. |
| 2016/0183841 A1 | 6/2016 | Duindam et al. |
| 2016/0202053 A1 | 7/2016 | Walker et al. |
| 2016/0206389 A1 | 7/2016 | Miller |
| 2016/0213884 A1 | 7/2016 | Park |
| 2016/0228032 A1 | 8/2016 | Walker et al. |
| 2016/0270865 A1 | 9/2016 | Landey et al. |
| 2016/0278865 A1 | 9/2016 | Capote |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0331469 A1 | 11/2016 | Hall et al. |
| 2016/0338787 A1 | 11/2016 | Popovic |
| 2016/0346038 A1 | 12/2016 | Helgeson |
| 2016/0346924 A1 | 12/2016 | Hasegawa |
| 2016/0354057 A1 | 12/2016 | Hansen et al. |
| 2016/0360947 A1 | 12/2016 | Iida |
| 2016/0360949 A1 | 12/2016 | Hyodo |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0065356 A1 | 3/2017 | Balaji et al. |
| 2017/0065364 A1 | 3/2017 | Schuh et al. |
| 2017/0065365 A1 | 3/2017 | Schuh |
| 2017/0068796 A1 | 3/2017 | Passerini et al. |
| 2017/0100084 A1 | 4/2017 | Walker et al. |
| 2017/0100197 A1 | 4/2017 | Zubiate |
| 2017/0100199 A1 | 4/2017 | Yu et al. |
| 2017/0105803 A1 | 4/2017 | Wong et al. |
| 2017/0106904 A1 | 4/2017 | Hanson |
| 2017/0113019 A1 | 4/2017 | Wong et al. |
| 2017/0119413 A1 | 5/2017 | Romo |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0245854 A1 | 8/2017 | Zemlok |
| 2017/0245885 A1 | 8/2017 | Lenker |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0303889 A1 | 10/2017 | Grim |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0064498 A1 | 3/2018 | Kapadia |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0167367 A1 | 6/2019 | Walker et al. |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0008874 A1 | 1/2020 | Barbagli et al. |
| 2020/0022767 A1 | 1/2020 | Hill |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |

(56) References Cited

U.S. PATENT DOCUMENTS

| | | |
|---|---|---|
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0246591 A1 | 8/2020 | Bogusky |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 1846181 | 10/2006 |
| CN | 1857877 | 11/2006 |
| CN | 101325920 | 12/2008 |
| CN | 102316817 | 1/2012 |
| CN | 102458295 | 5/2012 |
| CN | 102711586 | 10/2012 |
| CN | 102973317 | 3/2013 |
| CN | 103565529 | 2/2014 |
| CN | 103735313 | 4/2014 |
| CN | 103767659 | 5/2014 |
| CN | 103930063 | 7/2014 |
| CN | 104684502 | 6/2015 |
| CN | 105030331 | 11/2015 |
| CN | 105559850 | 5/2016 |
| CN | 105559886 | 5/2016 |
| CN | 105611881 | 5/2016 |
| CN | 107028659 | 8/2017 |
| CN | 104931059 | 9/2018 |
| DE | 102013100605 | 7/2014 |
| EP | 1 250 986 | 10/2002 |
| EP | 1 566 150 | 8/2005 |
| EP | 1 800 593 | 6/2007 |
| EP | 2 158 834 | 3/2010 |
| EP | 2 392 435 | 12/2011 |
| EP | 3 025 630 | 6/2016 |
| JP | 2008-528130 | 7/2008 |
| JP | 2009-509654 | 3/2009 |
| JP | 2009-524530 | 7/2009 |
| JP | 2011-088260 | 5/2011 |
| JP | 2013-510662 | 3/2013 |
| JP | 2014236971 A | 12/2014 |
| JP | 2014533996 A | 12/2014 |
| JP | 2015024032 A | 2/2015 |
| JP | 2015535191 A | 12/2015 |
| JP | 2018515299 A | 6/2018 |
| RU | 2569699 C2 | 11/2015 |
| WO | WO 01/56457 | 8/2001 |
| WO | WO 04/029782 | 4/2004 |
| WO | WO 05/087128 | 9/2005 |
| WO | WO 06/122061 | 11/2006 |
| WO | WO 09/120940 | 10/2009 |
| WO | WO 11/132409 | 10/2011 |
| WO | WO 12/044334 | 4/2012 |
| WO | 2013056006 A2 | 4/2013 |
| WO | WO 14/114551 | 7/2014 |
| WO | WO 15/142957 | 9/2015 |
| WO | WO 17/048194 | 3/2017 |
| WO | 2019005872 A1 | 1/2019 |

OTHER PUBLICATIONS

Verdaasdonk et al., Jan. 23, 2012, Effect of microsecond pulse length and tip shape on explosive bubble formation of 2.78 µm Er,Cr;YSGG and 2.94 µm Er:YAG laser, Proceedings of SPIE, vol. 8221, 12.

International Search Report and Written Opinion dated Nov. 5, 2018 in application No. PCT/US18/39793.

Blankenstein, Jun. 2008, Dynamic Registration and High Speed Visual Servoing in Robot-Assisted Surgery, Katholieke Universiteit Leuven, Leuven, Belgium.

Lawton et al., 1999, Ribbons and groups: A thin rod theory for catheters and filaments, J. Phys. A., 1999, 32:1709-1735.

European Search Report dated Feb. 25, 2021 for EP Patent Appl. No 18824749.8, 8 pages.

Final Rejection for U.S. Appl. No. 15/640,277, dated Jul. 20, 2018, 12 pages.

Non-Final Rejection for U.S. Appl. No. 15/640,277, dated Mar. 5, 2018, 8 pages.

Notice of Allowance for U.S. Appl. No. 15/640,277, dated May 20, 2019, 7 pages.

CN 1st Office Action for appl No. 201880044223.4, dated Jan. 18, 2022, 12 pages.

JP Office Action for Appl. No. 2019571227, dated May 10, 2022, 7 pages.

JP Office Action for Appl. No. 2022145960, dated Nov. 22, 2022, 7 pages.

KR Office Action for KR Appl. No. 10-2020-7002803, dated Nov. 8, 2022, 8 pages.

\* cited by examiner

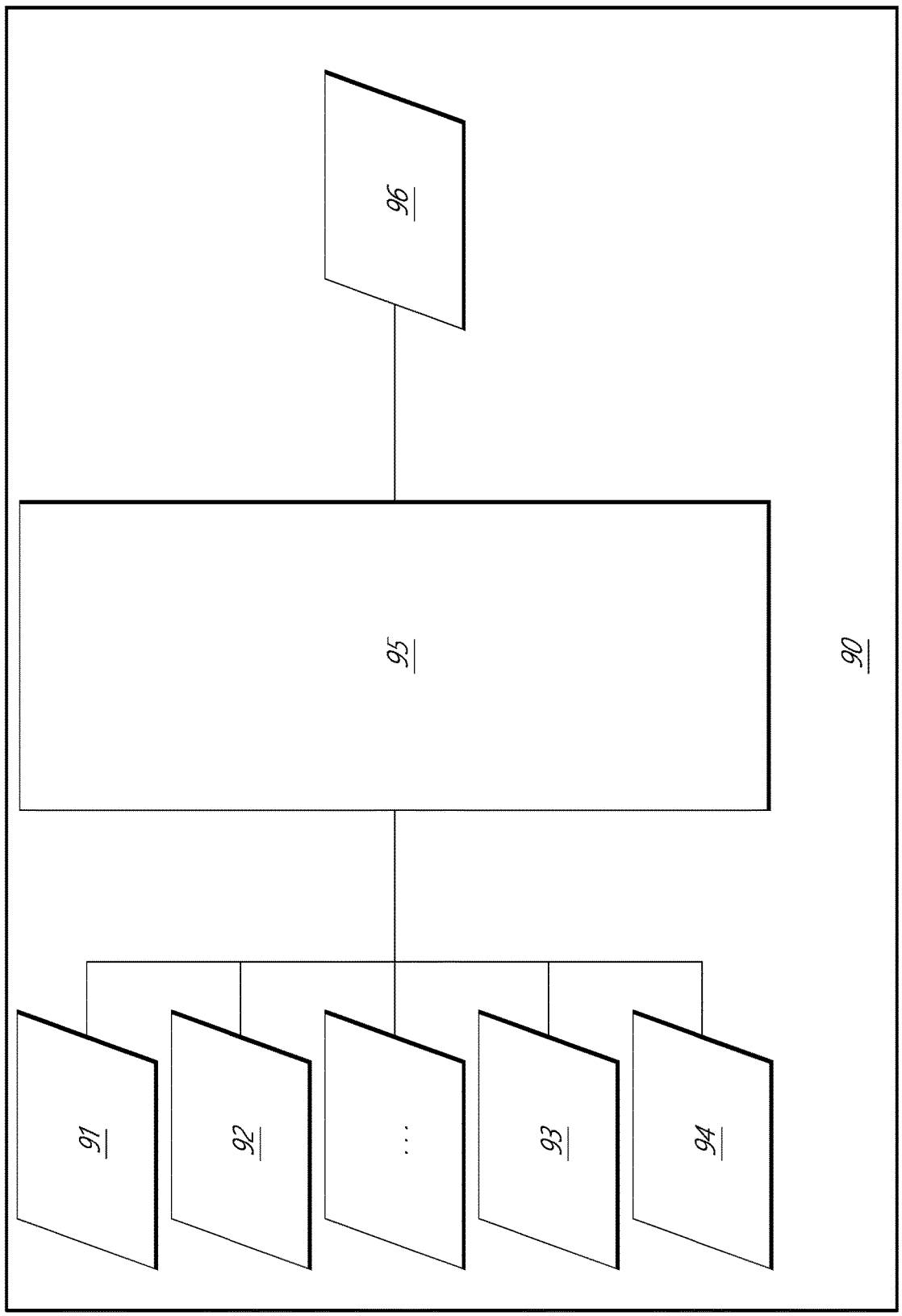

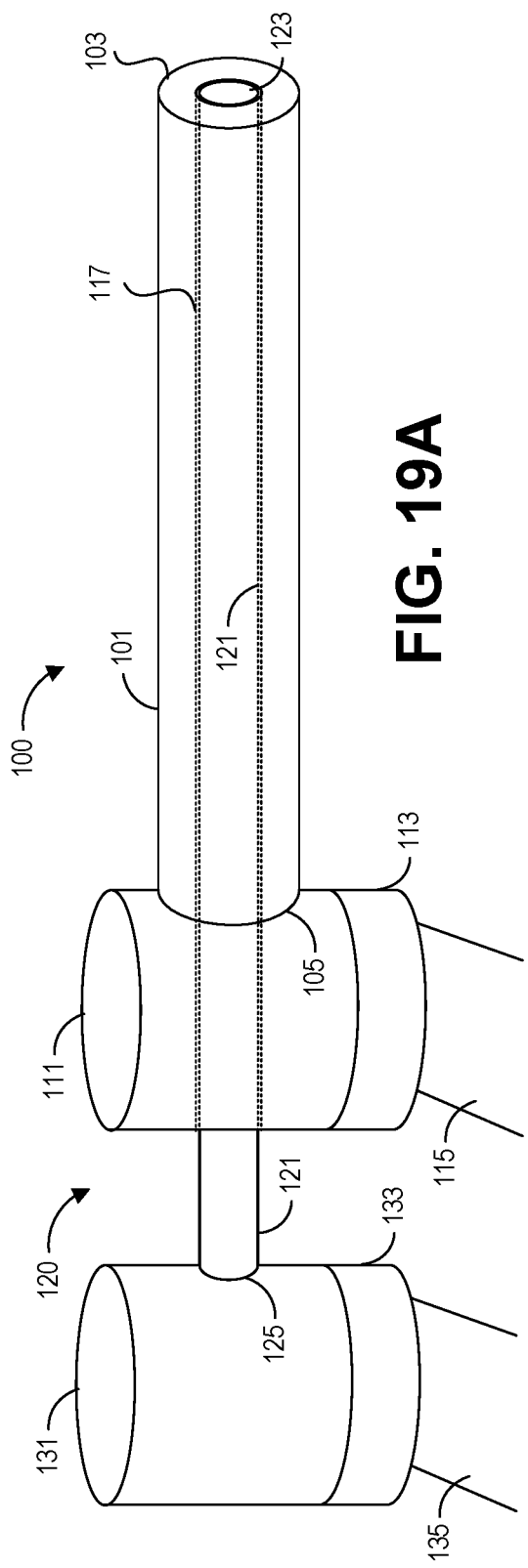
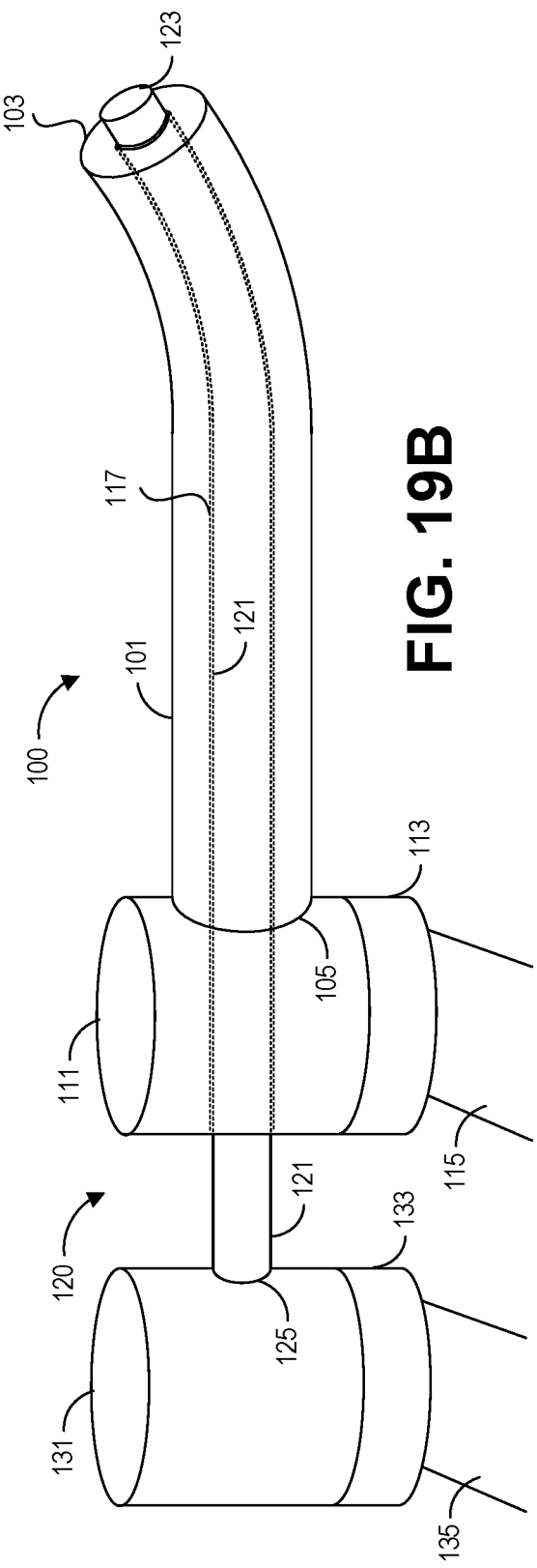

SYSTEMS AND METHODS FOR MEDICAL INSTRUMENT COMPRESSION COMPENSATION

CROSS-REFERENCE TO RELATED APPLICATION(S)

This application is a divisional of application Ser. No. 15/640,277, filed Jun. 30, 2017, which is hereby incorporated by reference in its entirety.

TECHNICAL FIELD

The systems and methods disclosed herein are directed to medical instruments, and more particularly to systems and methods that compensate for compression of elongated shafts of the medical instruments.

BACKGROUND

Medical procedures may involve accessing and visualizing an internal region of a patient for diagnostic or therapeutic purposes. Endoscopy, for example, may include accessing and visualizing the inside of a patient's lumen (e.g., airways). As another example, laparoscopy may include accessing and visualizing an internal cavity of a patient. During a procedure, a medical instrument such as, for example, a scope, may be inserted into the patient's body and an instrument can be passed through the scope to a tissue site identified for diagnosis and/or treatment.

In some instances, the medical instrument can include an elongated shaft (or an elongated body generally) that is steerable or articulable so as to navigate an interior region of the patient. In some instances, the medical instrument can be robotically controlled.

SUMMARY

The systems, techniques and devices of this disclosure each have several innovative aspects, no single one of which is solely responsible for the desirable attributes disclosed herein.

In some instances, medical instruments include elongated shafts configured for insertion into a body of a patient. The elongated shafts can be articulable so that they can be navigated within the patient. The elongated shafts can include pull wires that are actuable to articulate the elongated shafts. Pull wire-based movements (i.e., movements caused by actuating the pull wires) may cause undesirable compression (e.g., axial compression) of the elongated shafts. The systems and methods of the present disclosure can compensate for this compression by determining the amount of the compression and moving (e.g., advancing) the medical instrument with an instrument positioning device (e.g., a robotic arm) to compensate for the compression.

In some instances, a compression compensation parameter is used to determine the compression of the elongated shaft of the medical instrument. The compression compensation parameter can relate a characteristic of pull wire-based movement (e.g., pull wire tension, pull wire displacement, actuator displacement, commanded angle of articulation, measured angle of articulation, etc.) to axial compression. The compression compensation parameter can be determined during a calibration process of the medical instrument. The compression compensation parameter can be stored in a memory (e.g., non-transitory computer readable medium) on the medical instrument.

Accordingly, a first aspect of the disclosure relates to a medical instrument. The medical instrument includes an elongated shaft extending between a distal portion and a proximal portion. The elongated shaft is configured for insertion, in use, into a lumen of a patient. The medical instrument also includes an instrument base connected to the proximal portion of the elongated shaft. The instrument base includes an attachment interface configured to facilitate attachment to a robotic arm. The medical instrument also includes a non-transitory computer readable medium storing a compression compensation parameter that relates movement of the elongated shaft to axial compression of the elongated shaft. The medical instrument also includes a pull wire connected to the distal portion of the elongated shaft. The pull wire extends along the elongated shaft between the distal portion and a drive input positioned at the instrument base. The drive input configured to actuate the pull wire to cause movement of the elongated shaft based at least in part on the stored compression compensation parameter.

The medical instrument of the first aspect may include one or more of the following features, in any combination: (a) movement of the elongated shaft comprises articulation of the elongated shaft, and the compression compensation parameter relates an angle of articulation of the elongated shaft to an axial length of compression of the elongated shaft; (b) the angle of articulation comprises a commanded angle of articulation; (c) the angle of articulation comprises a measured angle of articulation; (d) at least one electromagnetic (EM) sensor is positioned on the elongated shaft, and the measured angle of articulation is determined based on a signal from the EM sensor; (e) a shape-sensing fiber is included on the elongated shaft, and the measured angle of articulation is determined based on the shape-sensing fiber; (f) at least one tension sensor is connected to the pull wire; (g) the compression compensation parameter relates a tension in the pull wire, as measured by the tension sensor, to an axial length of compression of the elongated shaft; (h) the compression compensation parameter relates a pull wire displacement to an axial length of compression of the elongated shaft; (i) the drive input comprises a pulley, and the compression compensation parameter relates a rotation of the pulley to an axial length of compression of the elongated shaft; (j) the drive input comprises at least one of a lever, a trigger, a crank, and a cam; (k) the drive input comprises a linear drive input, and the compression compensation parameter relates a linear displacement of a portion of the linear drive input to an axial length of compression of the elongated shaft; (l) the compression compensation parameter is determined during a calibration process of the medical instrument; (m) the non-transitory computer readable medium comprises a radio frequency identification (RFID) tag; (n) the RFID tag is positioned at the instrument base; (o) the RFID tag is configured to communicate the compression compensation parameter when activated by a RFID reader of the robotic arm; (p) the elongated shaft comprises an endoscope; (q) the elongated shaft comprises a sheath having a channel formed therethrough, the channel extending along an axis of the sheath; and/or (r) one or more additional pull wires.

In a second aspect, the disclosure relates to a robotic system. The robotic system includes a first medical instrument configured for insertion, in use, into a lumen of a patient. The first instrument includes: a first elongated shaft, a first pull wire actuable to cause pull wire-based movement of the first elongated shaft, and a first instrument base including a first drive input for actuating the first pull wire. The system includes a first instrument positioning device attached to the first instrument base and configured to move to advance or retract the first instrument through the lumen of the patient. The system includes at least one non-transitory computer readable medium having stored thereon executable instructions. The system also includes at least one processor in communication with the at least one non-transitory computer readable medium and configured to execute the instructions to cause the system to at least: determine an axial compression of the first elongated shaft; and move the first instrument positioning device to either advance or retract the first elongated shaft of the first instrument through the lumen of the patient to compensate for the determined axial compression of the first elongated shaft.

The robotic system of the second aspect may include one or more of the following features, in any combination: (a) the instructions cause the at least one processor to determine the axial compression of the first elongated shaft using a compression compensation parameter that relates pull wire-based movement of the first elongated shaft to axial compression of the first elongated shaft; (b) the pull wire-based movement causes articulation of the elongated shaft, and the compression compensation parameter relates an angle of articulation of the elongated shaft to an axial length of compression of the elongated shaft; (c) the angle of articulation comprises a commanded angle of articulation; (d) the angle of articulation comprises a measured angle of articulation; (e) at least one EM sensor positioned on the first elongated shaft, wherein the measured angle of articulation is determined based on a signal from the EM sensor; (f) a shape-sensing fiber on the first elongated shaft, and wherein the measured angle of articulation is determined based on the shape-sensing fiber; (g) the compression compensation parameter is determined during a calibration process of the first medical instrument; (h) an RFID tag on the first medical instrument, the RFID tag storing the compression compensation parameter, and an RFID reader connected to the at least one processor; (i) the RFID tag is positioned on the first instrument base, and the RFID reader is positioned on the first instrument positioning device; (j) the first medical instrument comprises an endoscope; (k) the first medical instrument comprises a sheath; (l) a second medical instrument configured for insertion through a working channel of the first instrument into the lumen of the patient, the second instrument comprising a second elongated shaft, a second pull wire actuable to articulate the second elongated shaft, and a second instrument base including a second drive input for actuating the second pull wire, a second instrument positioning device attached to the second instrument and configured to move to advance or retract the second instrument through the working channel of the first instrument, and wherein the instructions cause the at least one processor to move the second instrument positioning device to either advance or retract the second elongated shaft of the second medical instrument through the working channel of the first instrument; (m) the instructions cause the at least one processor to determine an axial compression of the second elongated shaft, and move the second instrument positioning device to either advance or retract the second elongated shaft of the second medical instrument through the working channel of the first medical instrument to compensate for the determined axial compression of the second elongated shaft; (n) the instructions cause the at least one processor to move the second instrument positioning device to either advance or retract the second elongated shaft of the second instrument through the working channel of the first medical instrument to compensate for the determined axial compression of the first elongated shaft; and/or (o) the first instrument comprises a sheath and the second instrument comprises an endoscope.

In a third aspect of the disclosure a robotic system includes a first medical instrument configured for insertion, in use, into a lumen of a patient. The first instrument includes a first elongated shaft, a first pull wire actuable to articulate the first elongated shaft, and a first instrument base including a first drive input for actuating the first pull wire. A first instrument positioning device is attached to the first instrument base and configured to move to advance or retract the first medical instrument through the lumen of the patient. The robotic system includes a second instrument configured for insertion through a working channel of the first medical instrument into the lumen of the patient. The second medical instrument includes a second elongated shaft, a second pull wire actuable to articulate the second elongated shaft, and a second instrument base including a second drive input for actuating the second pull wire. A second instrument positioning device is attached to the second instrument base and configured to move to advance or retract the second instrument through the working channel of the first instrument. The system also includes at least one non-transitory computer readable medium having stored thereon executable instructions, and at least one processor in communication with the at least one non-transitory computer readable medium and configured to execute the instructions to cause the system to at least: determine an axial compression of the first elongated shaft; move the first instrument positioning device to advance the first elongated shaft of the first medical instrument through the lumen of the patient to compensate for a first portion of the determined axial compression of the first elongated shaft; and move the second instrument positioning device to advance the second elongated shaft of the second medical instrument through the working channel of the first instrument to compensate for a second portion of the determined axial compression of the first elongated shaft. The second portion may be larger than the first portion.

In a fourth aspect, a robotic system includes a first medical instrument configured for insertion, in use, into a lumen of a patient. The first instrument includes a first elongated shaft, a first pull wire actuable to articulate the first elongated shaft, and a first instrument base including a first drive input for actuating the first pull wire. A first instrument positioning device is attached to the first instrument base and configured to move to advance or retract the first medical instrument through the lumen of the patient. The system also includes a second instrument configured for insertion through a working channel of the first medical instrument into the lumen of the patient. The second medical instrument includes a second elongated shaft, a second pull wire actuable to articulate the second elongated shaft, and a second instrument base including a second drive input for actuating the second pull wire. A second instrument positioning device is attached to the second instrument base and configured to move to advance or retract the second instrument through the working channel of the first instrument. The system also includes at least one non-transitory computer readable medium having stored thereon executable instructions, and at least one processor in communication with the at least one non-transitory computer readable medium and configured to execute the instructions to cause the system to at least: determine an axial compression of the second elongated shaft; move the first instrument positioning device to advance the first elongated shaft of the first medical instrument through the lumen of the patient to compensate for a first portion of the determined axial compression of the second elongated shaft; and move the second instrument positioning device to advance the second elongated shaft of the second medical instrument through the working channel of the first instrument to compensate for a second portion of the determined axial compression of the second elongated shaft. The second portion may be larger than the first portion.

In a fifth aspect of the disclosure, a non-transitory computer readable storage medium has stored thereon instructions that, when executed, cause a processor of a device to at least: determine, based at least in part on information indicative of a pull wire-based movement of an elongated shaft of a first medical instrument and a compression compensation parameter, an axial compression of the first elongated shaft of the first instrument; and move a first instrument positioning device connected to the first medical instrument to compensate for the axial compression of the first elongated shaft.

The non-transitory computer readable storage medium of the fifth aspect may include one or more of the following features, in any combination: (a) the information indicative of the pull-wire based movement comprises information indicative of a commanded articulation for the first medical instrument; (b) the information indicative of the pull-wire based movement comprises information indicative of a measured articulation for the first medical instrument; (c) the compression compensation parameter is determined during a calibration process of the first medical instrument; (d) the compression compensation parameter relates an angle of articulation of the first elongated shaft to an axial length of compression of the first elongated shaft; (e) the compression compensation parameter relates a tension in a pull wire of the first instrument to an axial length of compression of the first elongated shaft; (f) the compression compensation parameter relates a displacement of a pull wire of the first instrument to an axial length of compression of the first elongated shaft; (g) the compression compensation parameter relates a rotation of a pulley attached to a pull wire of the first instrument to an axial length of compression of the first elongated shaft; and/or (h) the instructions, when executed, cause the processor to move the first instrument positioning device to advance the elongated shaft of the first articulable medical instrument into a lumen of a patient.

In a sixth aspect of the disclosure, a method for calibrating a medical instrument comprising an articulable elongated shaft, includes: determining a pull wire-based movement for moving the elongated shaft to a first position; determining, with the elongated shaft in the first position, an axial compression of the elongated shaft; and determining, by relating the first position to the determined axial compression, a compression compensation parameter for the elongated shaft.

The method of the sixth aspect may also include one or more of the following features, in any combination: (a) articulating the elongated shaft to the first position; (b) articulating the elongated shaft comprises tensioning a pull wire connected to a distal portion of the elongated shaft; (c) wherein determining the pull wire-based movement comprises measuring a tension in the pull wire; (d) attaching one or more spatial caps to a distal portion of the elongated shaft, the one or more spatial caps configured to provide spatial data about the location and orientation of the distal portion of the elongated shaft, and wherein determining the pull wire-based movement comprises analyzing the spatial data; (e) wherein determining the axial compression comprises analyzing the spatial data; (f) wherein the elongated shaft comprises a spatial sensor configured to provide spatial data about the location and orientation of the distal portion of the elongated shaft, and wherein determining the pull wire-based movement comprises analyzing the spatial data; (g) wherein determining the axial compression comprises analyzing the spatial data; (h) wherein the one or more spatial caps comprise one or more EM sensors; (i) wherein determining the axial compression comprises measuring a length of the elongated shaft; (j) wherein determining the articulation comprises measuring an angle of the elongated shaft; and/or (k) storing the compression compensation parameter in a non-transitory computer readable medium of the first medical instrument.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 19A illustrates an example of a second medical instrument telescoping within a working channel of a first medical instrument.

FIG. 19B depicts an example of axial compression of the first and second medical instruments caused by pull wire-based movement.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System-Cart

Figure 1:
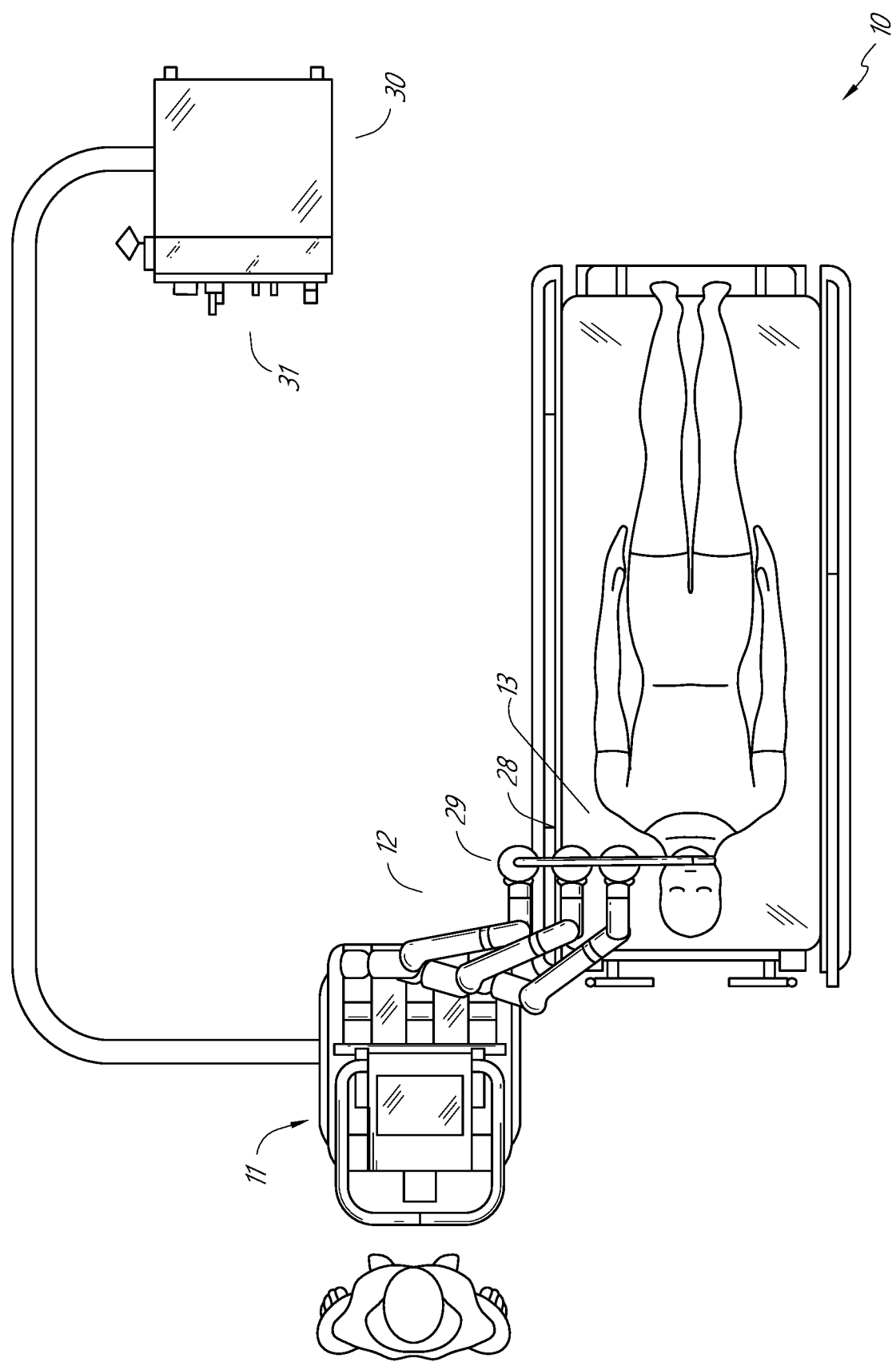
FIG. 1 illustrates an embodiment of a cart-based robotic system arranged for diagnostic and/or therapeutic bronchoscopy.
Figure 2:
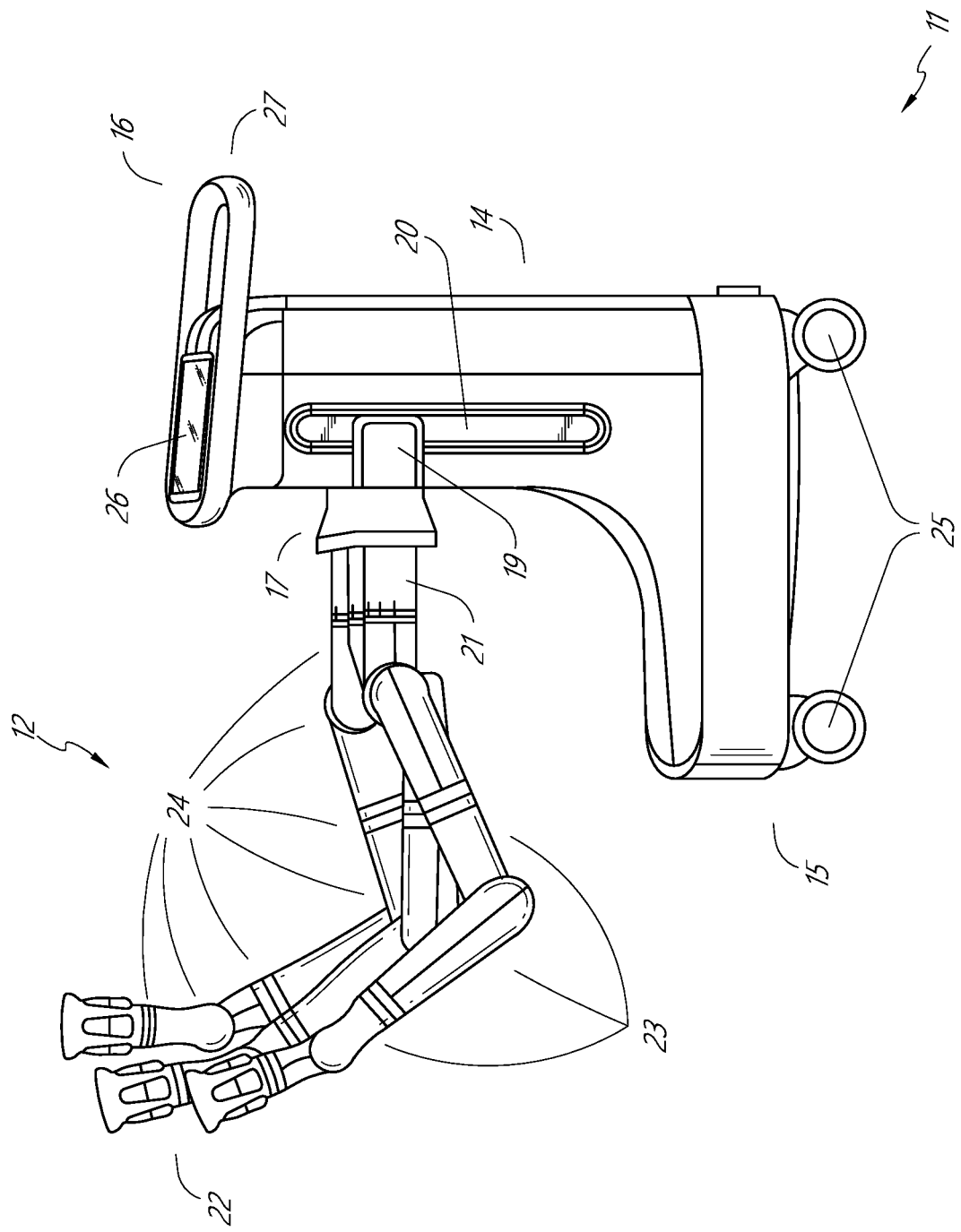
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments may need to be delivered in separate procedures. In those circumstances, the endoscope 13 may also be used to deliver a fiducial to "mark" the location of the target nodule as well.

In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position the physician may view the console 16, robotic arms 12, and patient while operating the console 16 from behind the cart 11. As shown, the console 16 also includes a handle 27 to assist with maneuvering and stabilizing the cart 11.

Figure 3:
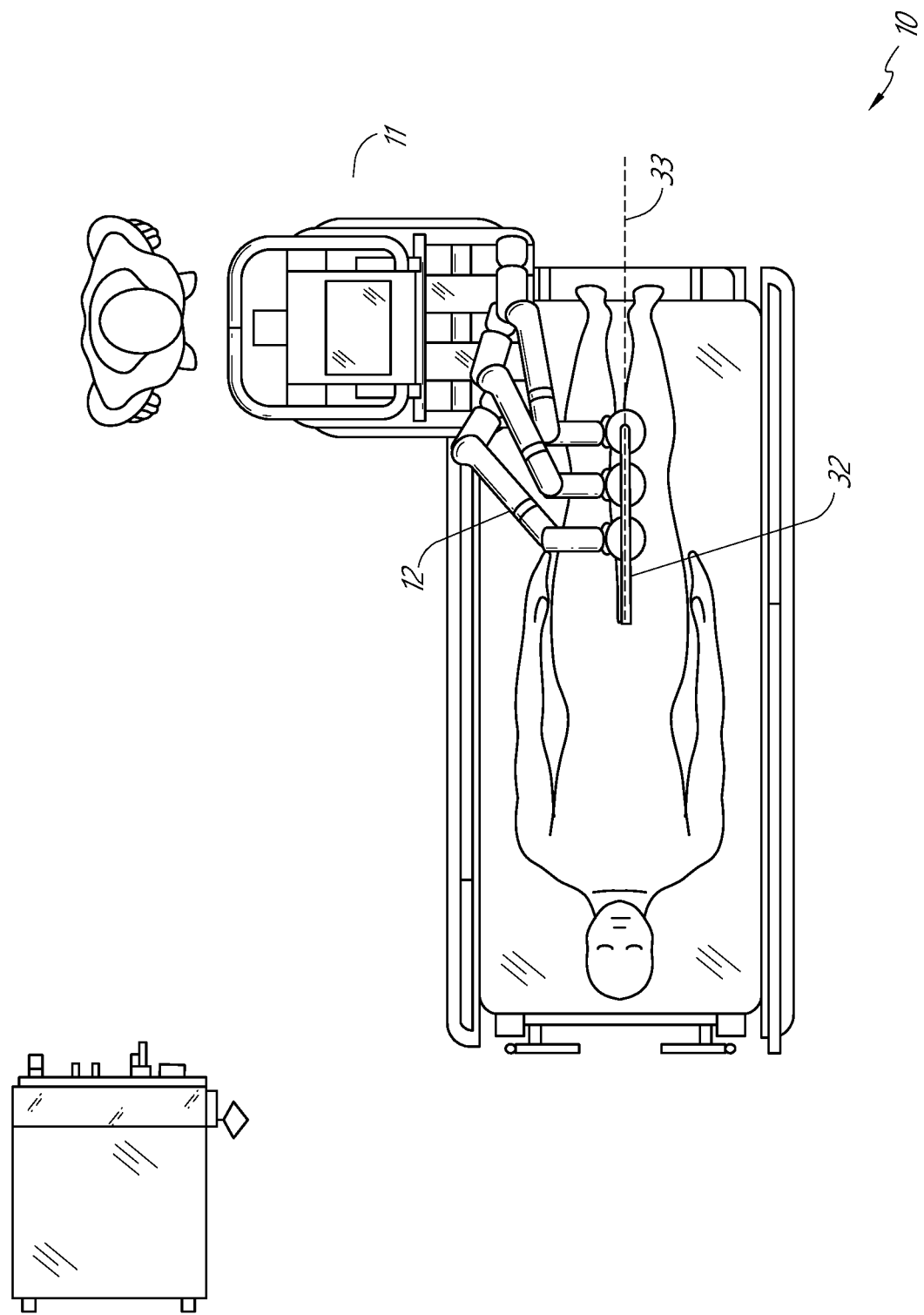
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using laser or ultrasonic lithotripsy device deployed down the working channel of the ureteroscope 32. After lithotripsy is complete, the resulting stone fragments may be removed using baskets deployed down the ureteroscope 32.

Figure 4:
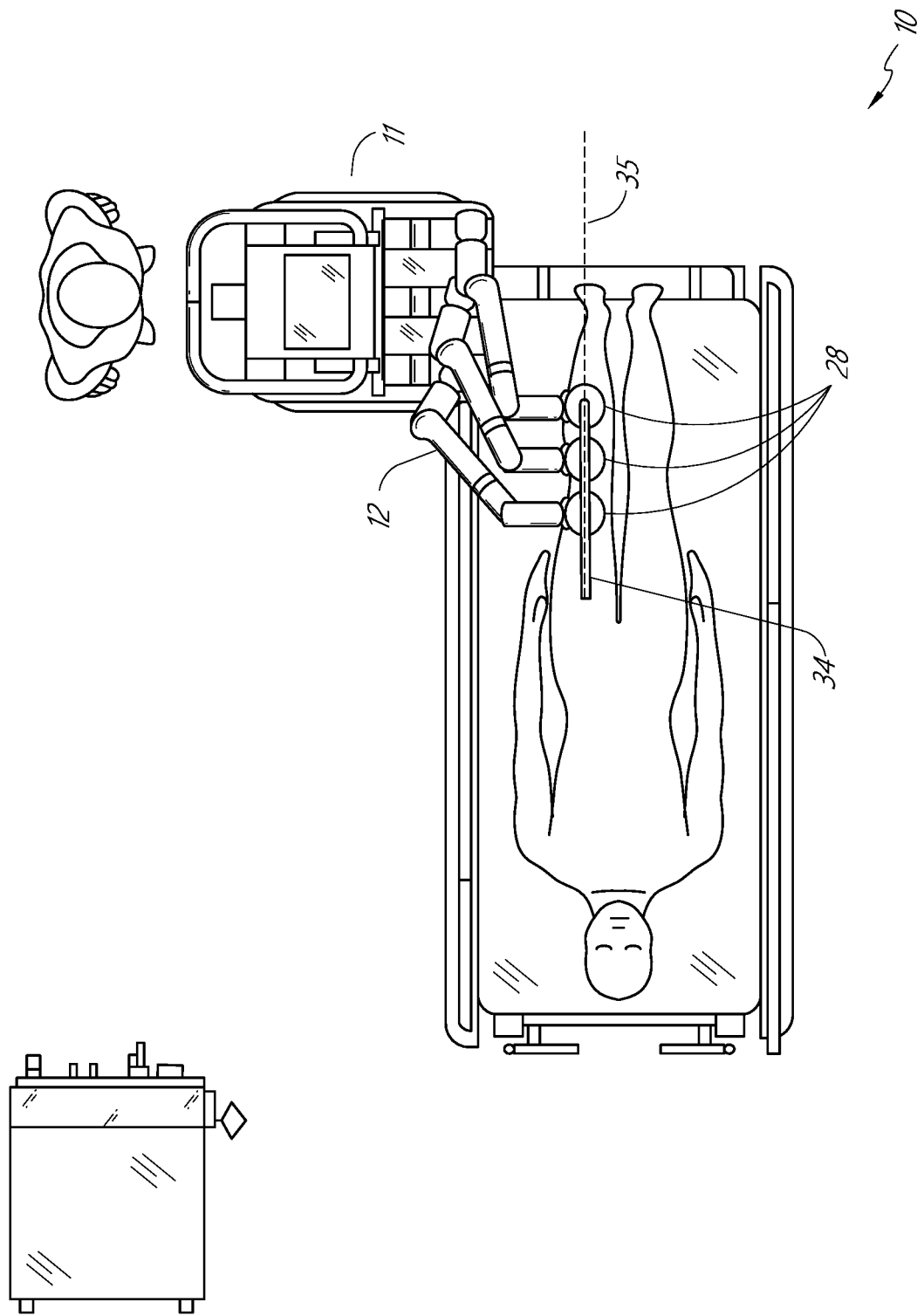
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System-Table

Figure 5:
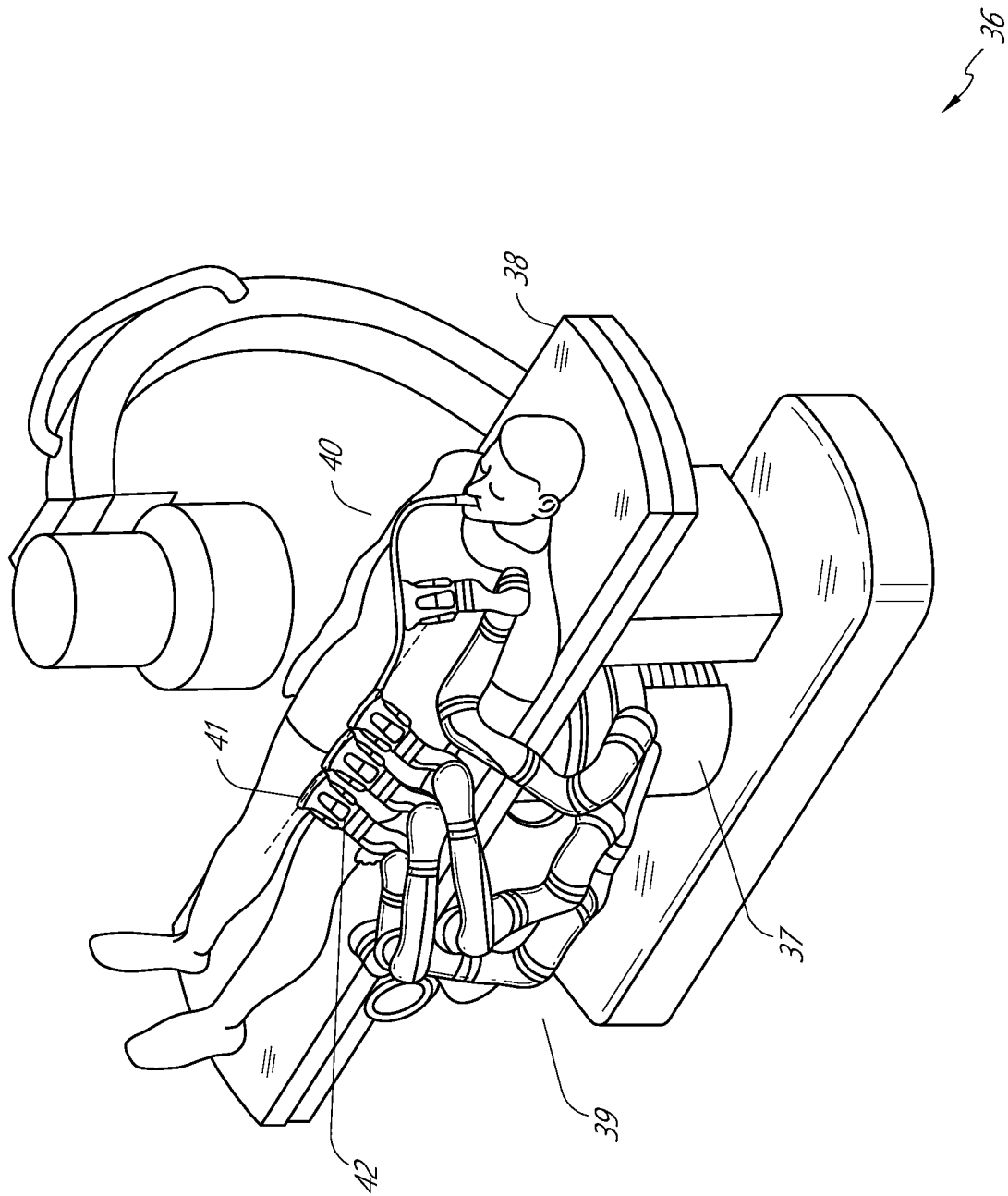
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
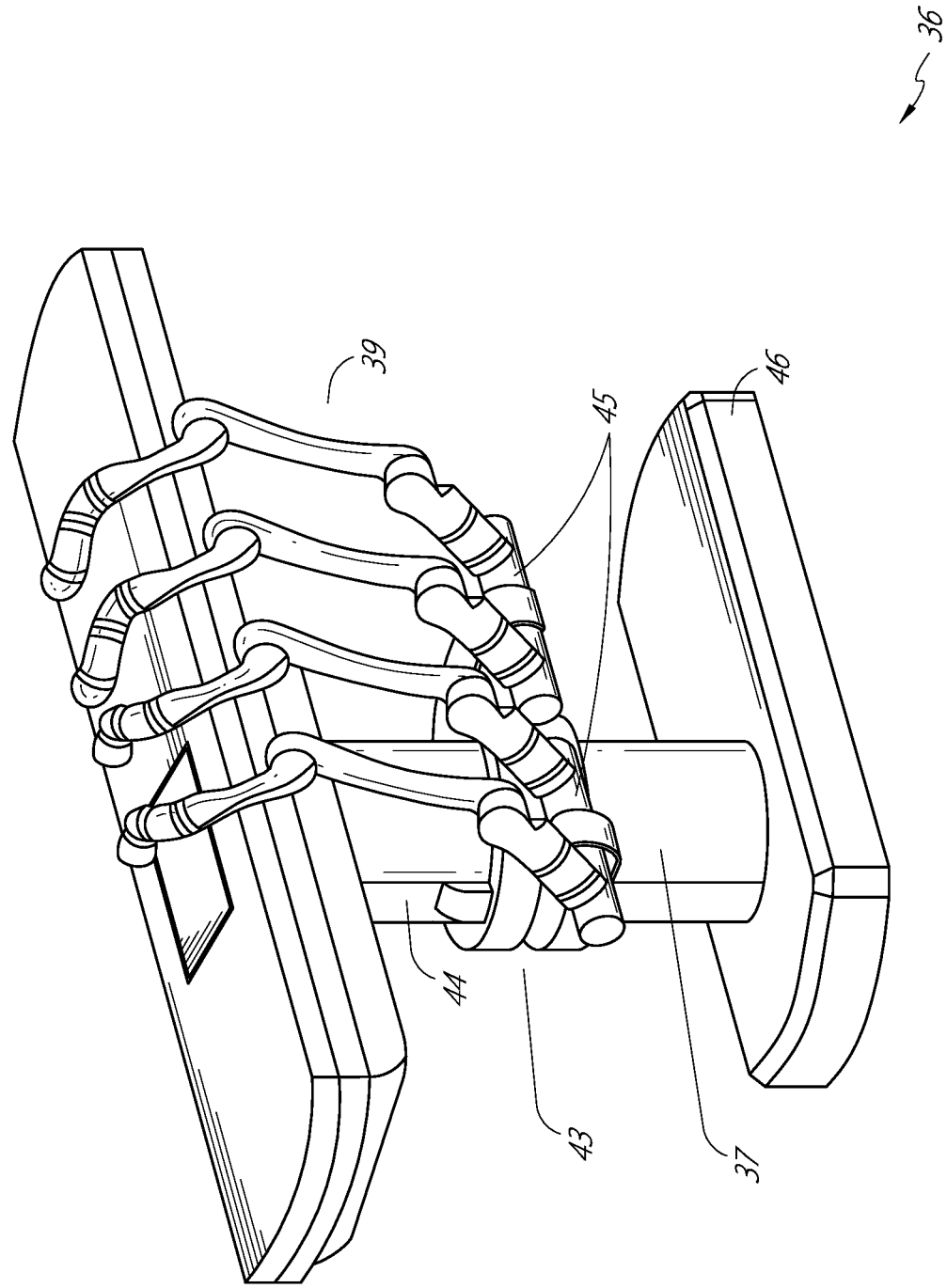
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient.

Figure 9:
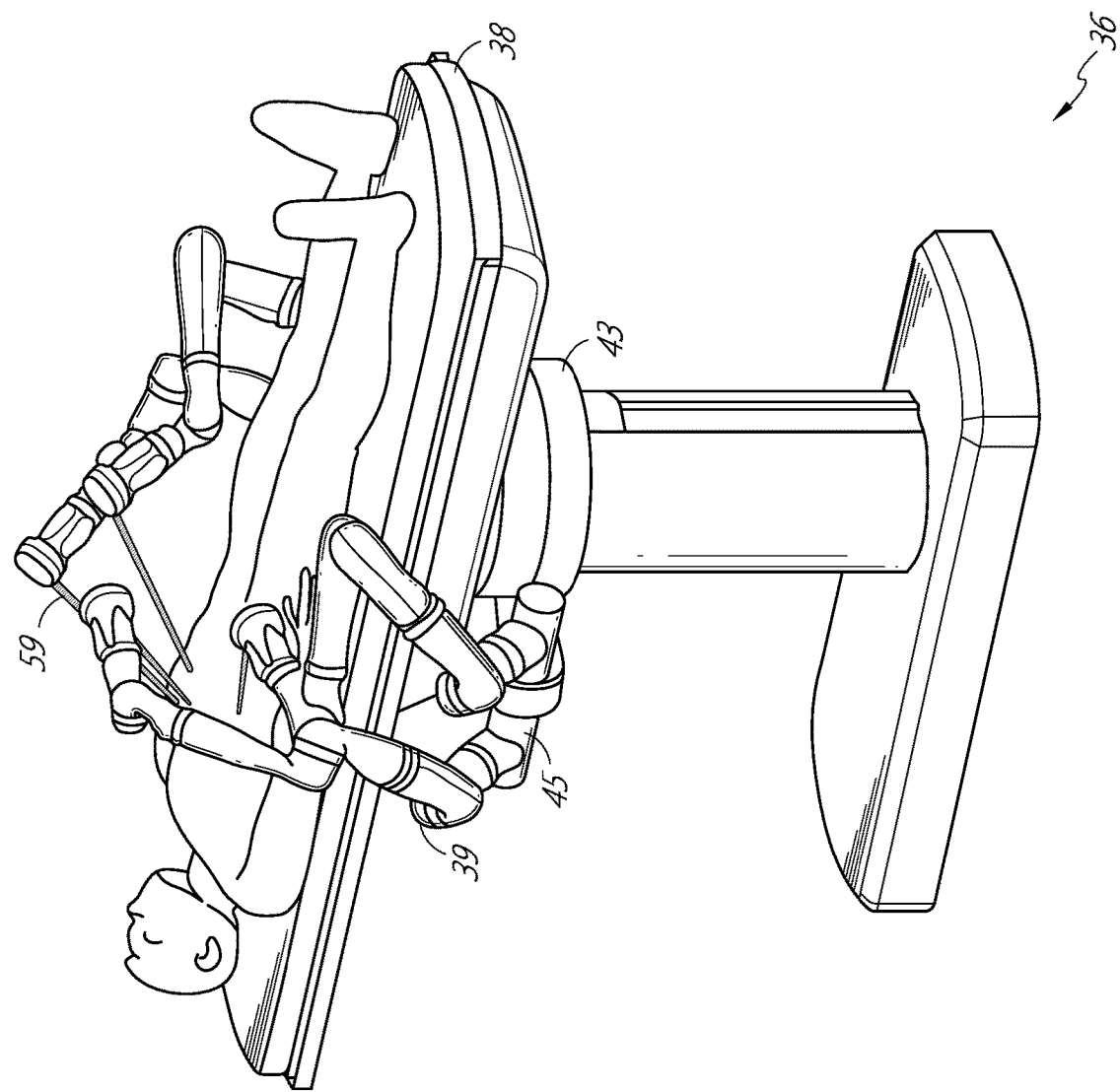
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may be provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a console that provides both a user interface for user input, such as keyboard and/or pendant, as well as a display screen (or touchscreen) for preoperative and intraoperative information, such as real-time imaging, navigation, and tracking information.

Figure 7:
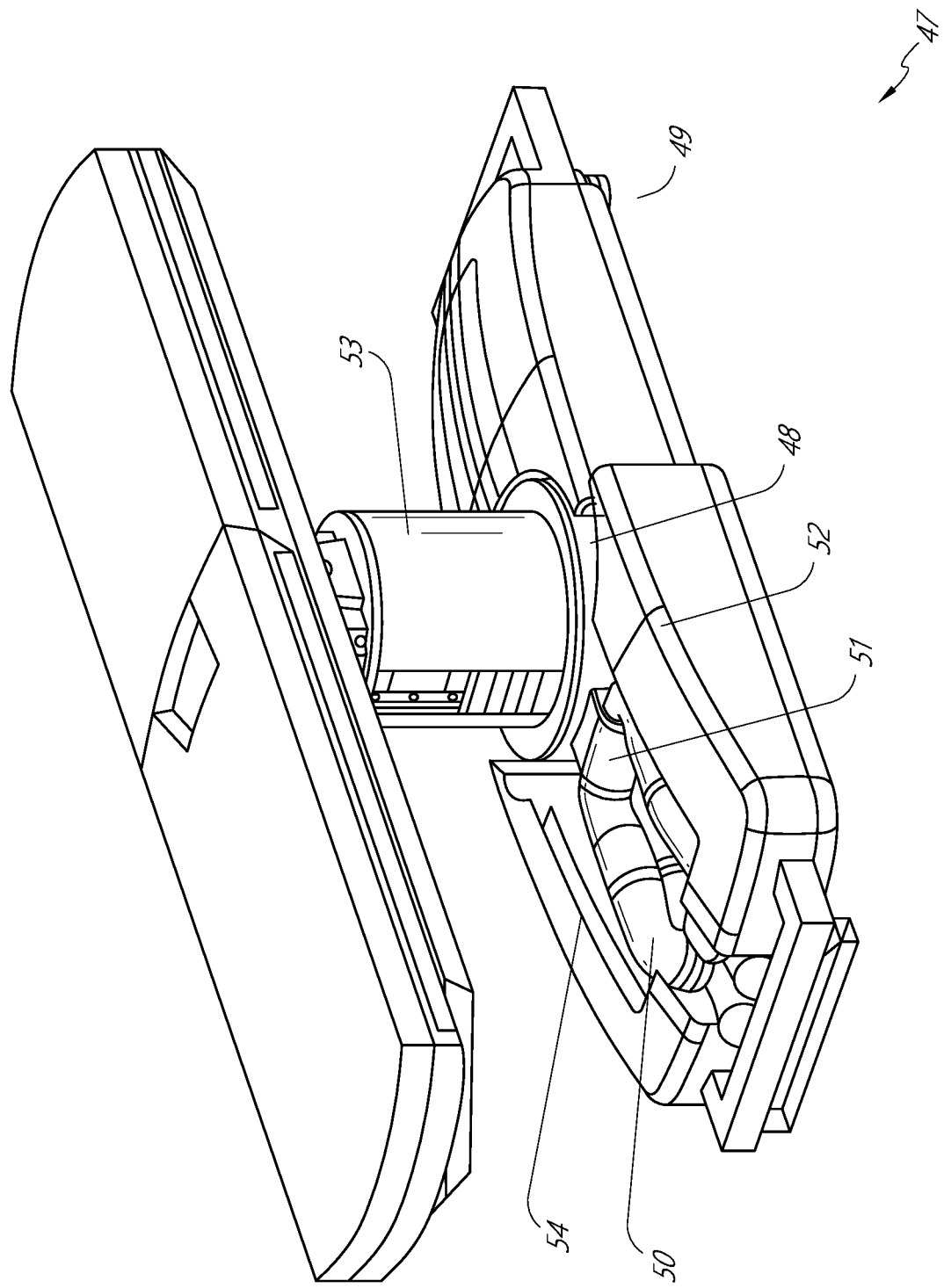
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
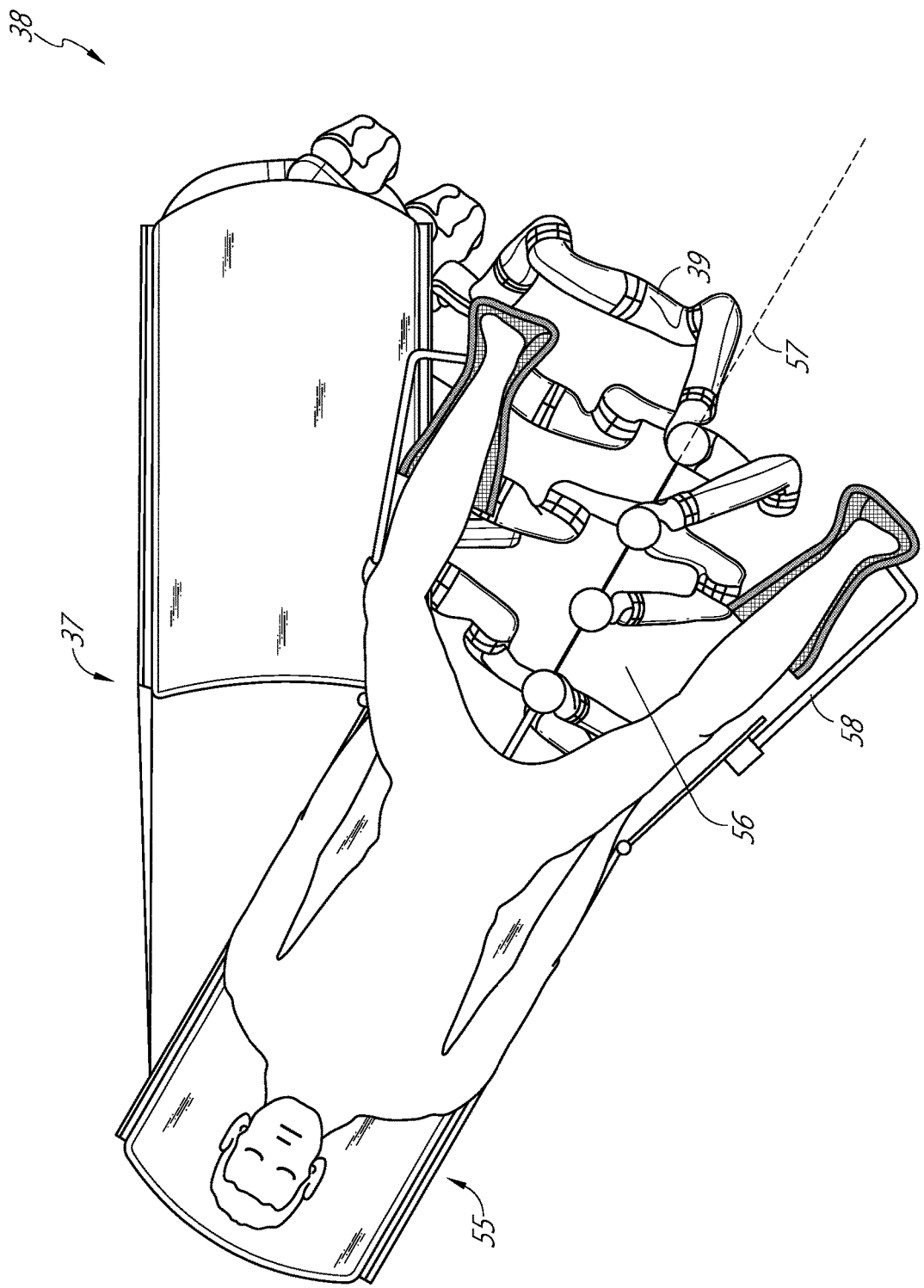
FIG. 8 illustrates an embodiment of a table-based robotic system configured for an ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments (elongated in shape to accommodate the size of the one or more incisions) may be inserted into the patient's anatomy. After inflation of the patient's abdominal cavity, the instruments, often referred to as laparoscopes, may be directed to perform surgical tasks, such as grasping, cutting, ablating, suturing, etc. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that laparoscopes 59 may be positioned using the arm mounts 45 to be passed through minimal incisions on both sides of the patient to reach his/her abdominal cavity.

Figure 10:
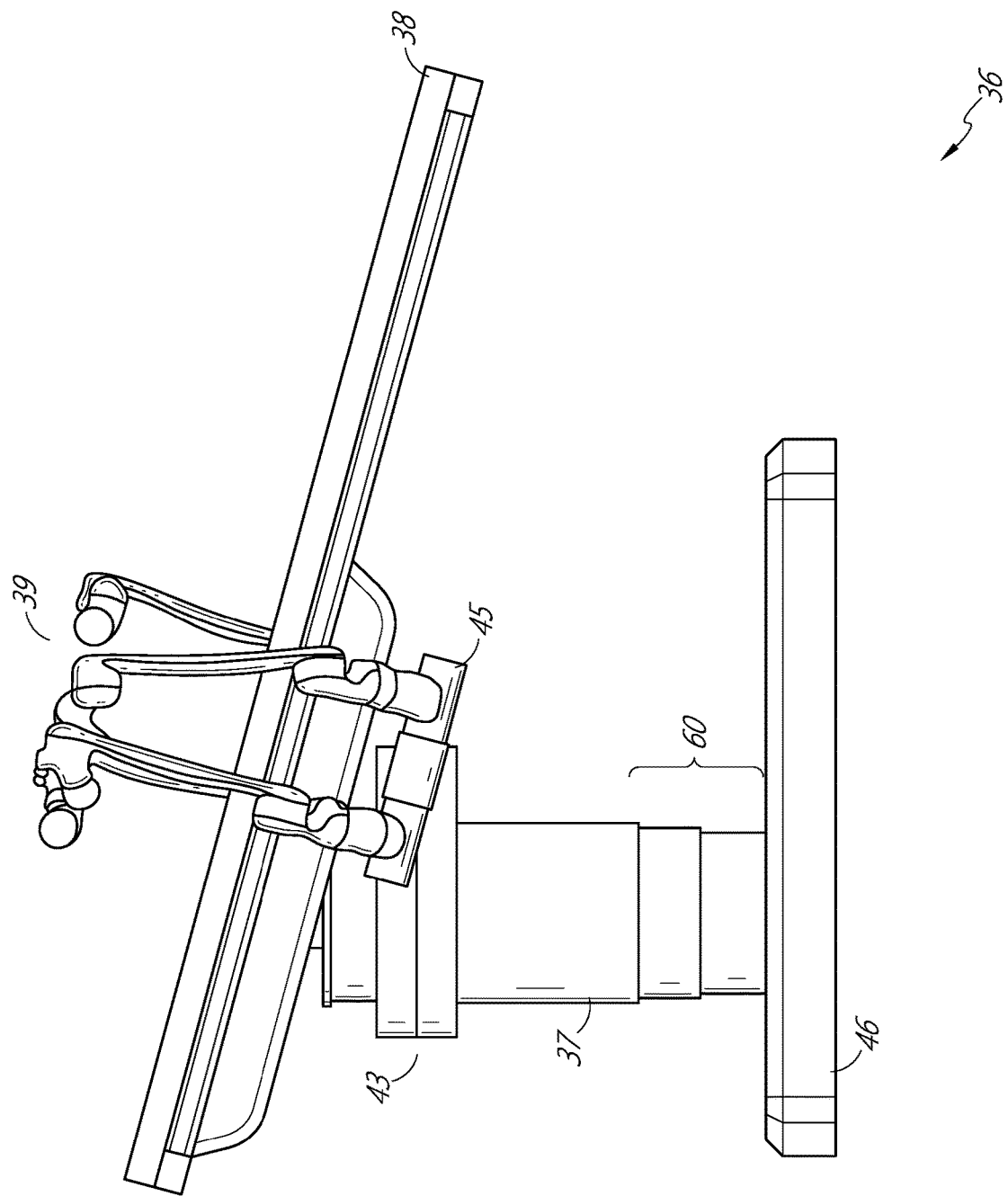
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
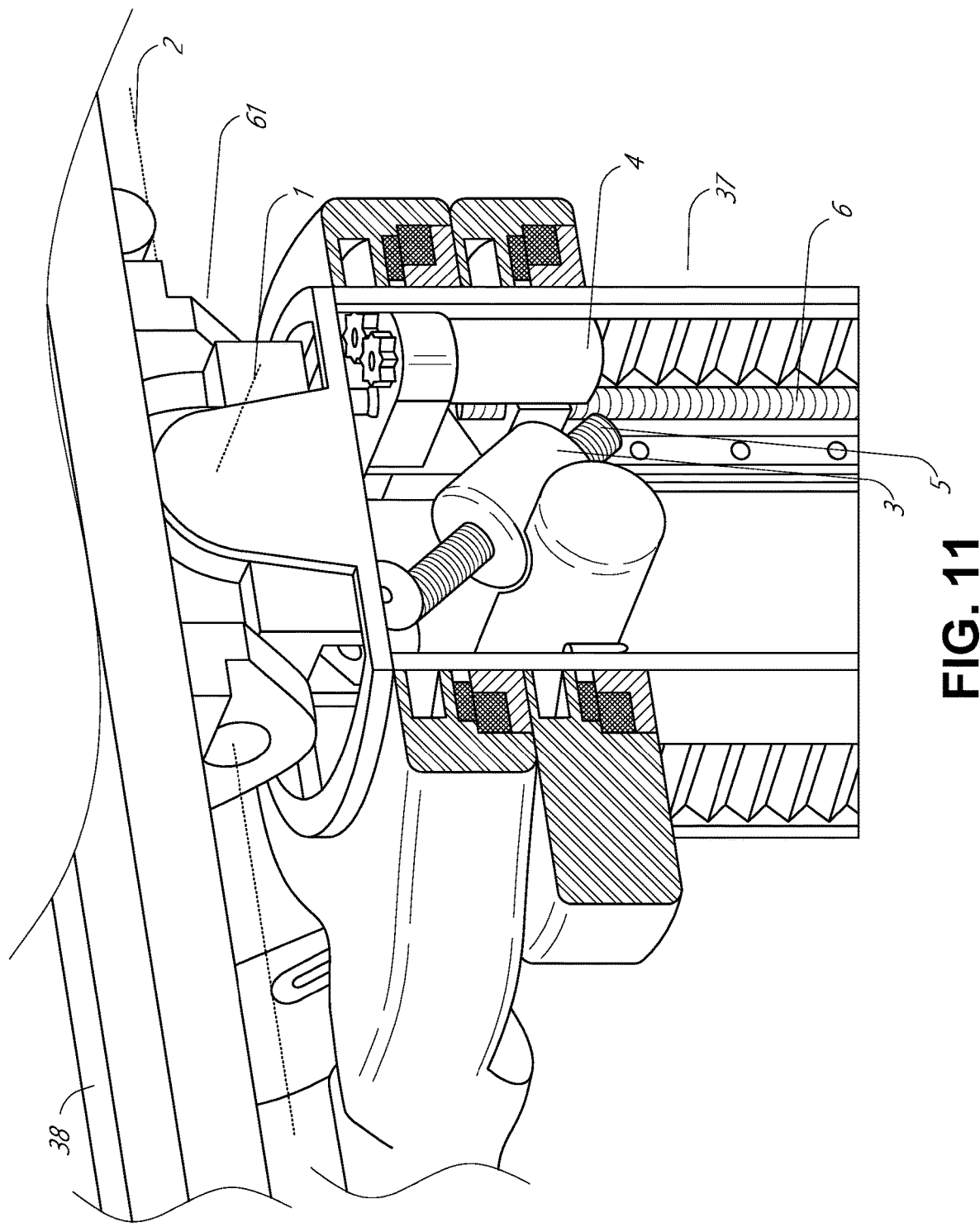
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 2, 4 responsive to an electrical pitch angle command. Rotation along one screw 5 would enable tilt adjustments in one axis 1, while rotation along the other screw 6 would enable tilt adjustments along the other axis 2.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical procedures, such as laparoscopic prostatectomy.

C. Instrument Driver & Interface

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
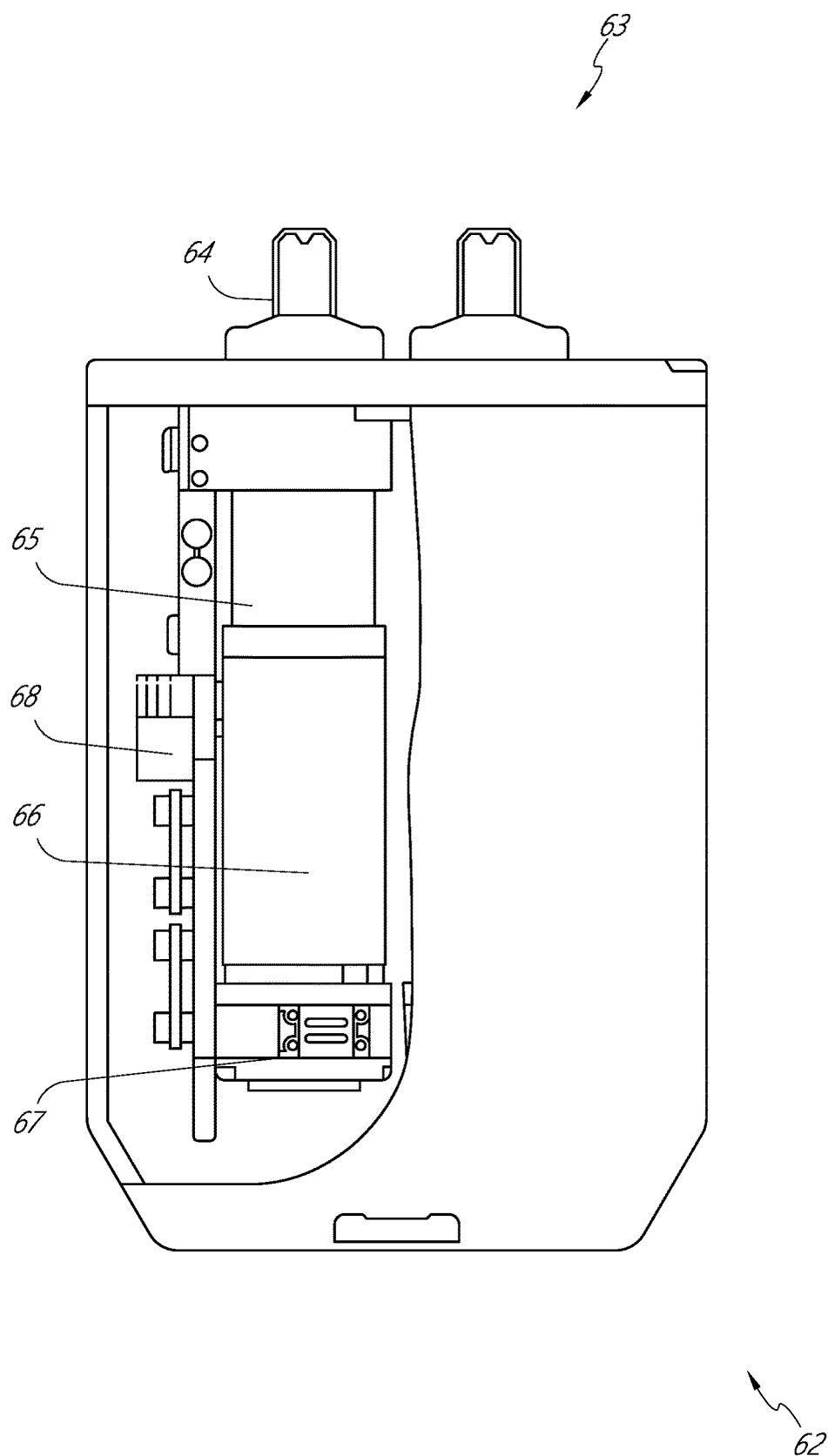
FIG. 12 illustrates an exemplary instrument driver.

FIG. 12 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (four as shown in FIG. 12) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

Figure 13:
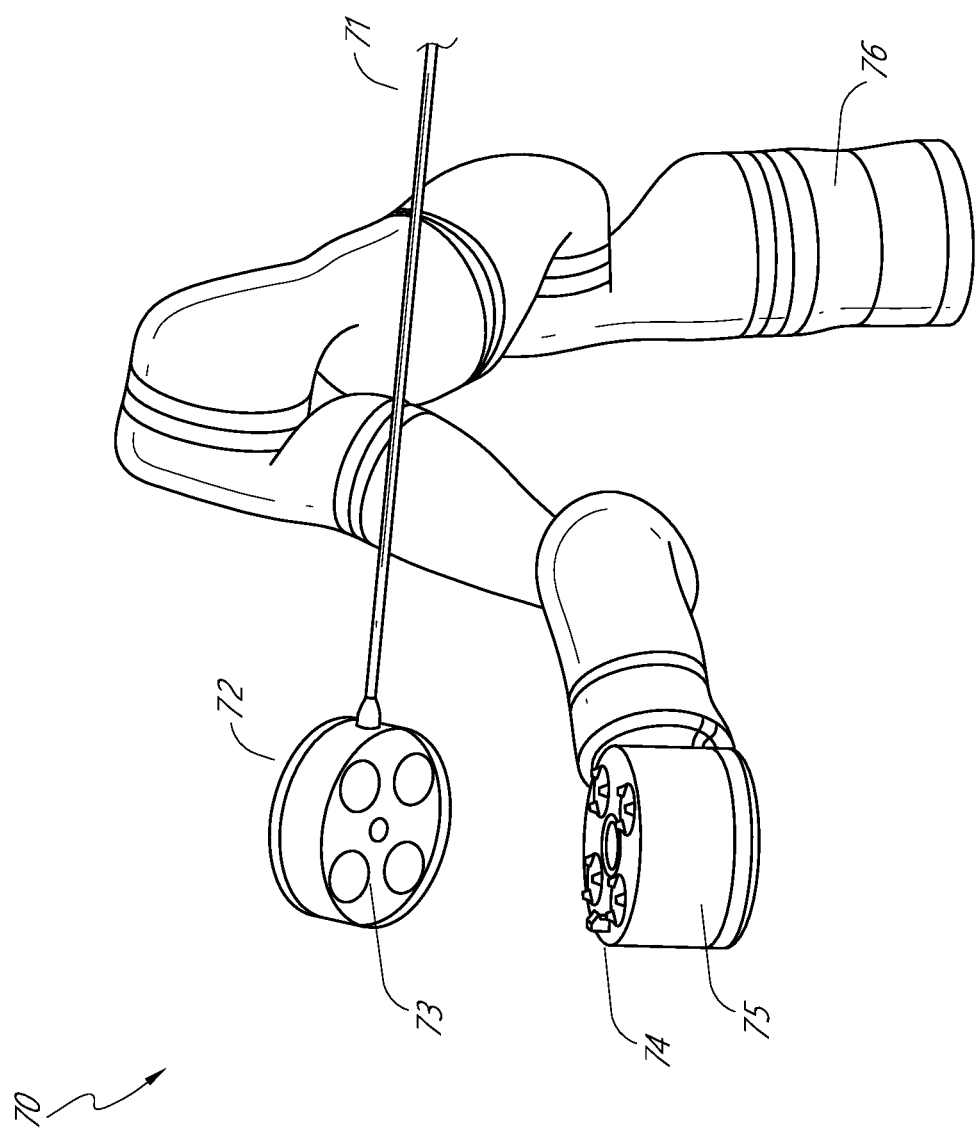
FIG. 13 illustrates an exemplary medical instrument with a paired instrument driver.

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 66 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons within the elongated shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control algorithms intended to predict movement of the flexible elongate shaft 71 during an endoscopic procedure.

Figure 14:
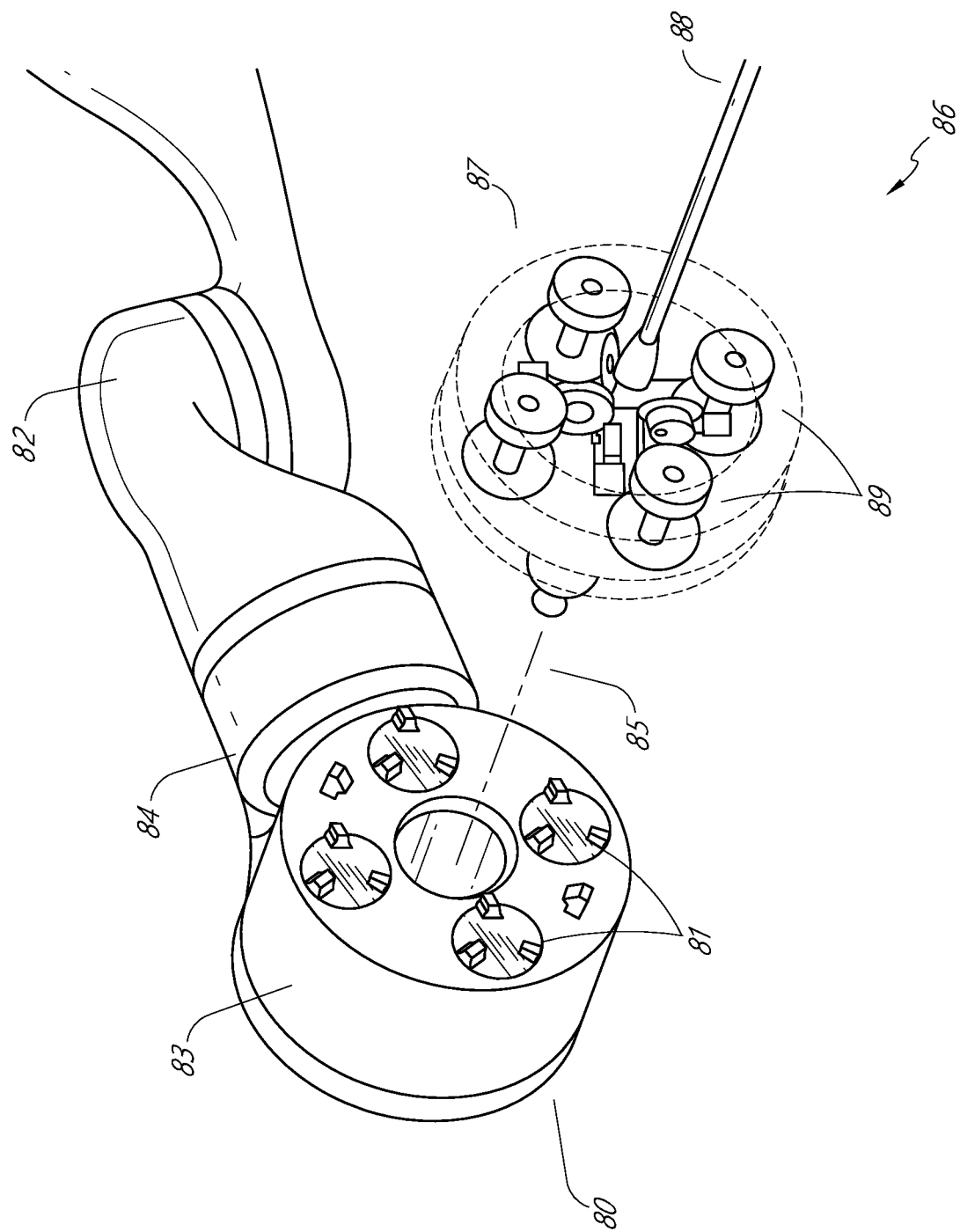
FIG. 14 illustrates an alternative design for an instrument driver and instrument where the axes of the drive units are parallel to the axis of the elongated shaft of the instrument.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise of an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image data) location tracking modules or features. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some feature of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Medical Instrument Compression Compensation

Embodiments of the disclosure relate to systems and techniques for compensating for compression of medical instruments. Medical instruments can include elongated shafts that experience compression when articulated. As described herein, the medical instruments can be attached to instrument positioning devices that are configured to move the medical instruments to compensate for this compression. For example, an instrument positioning device can advance a medical instrument to compensate for compression in an elongated shaft of the medical instrument. In some embodiments, the amount of compression is determined using one or more compression compensation parameters. The one or more compression compensation parameters can be determined during calibration of the medical instrument.

A. Compression of a Medical Instrument

Figure 16A:
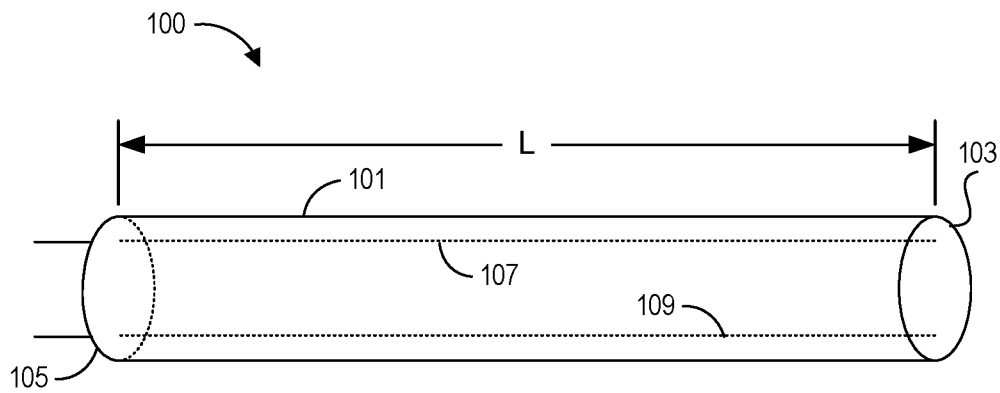
FIG. 16A illustrates an embodiment of an elongated shaft of a medical instrument.
Figure 17A:
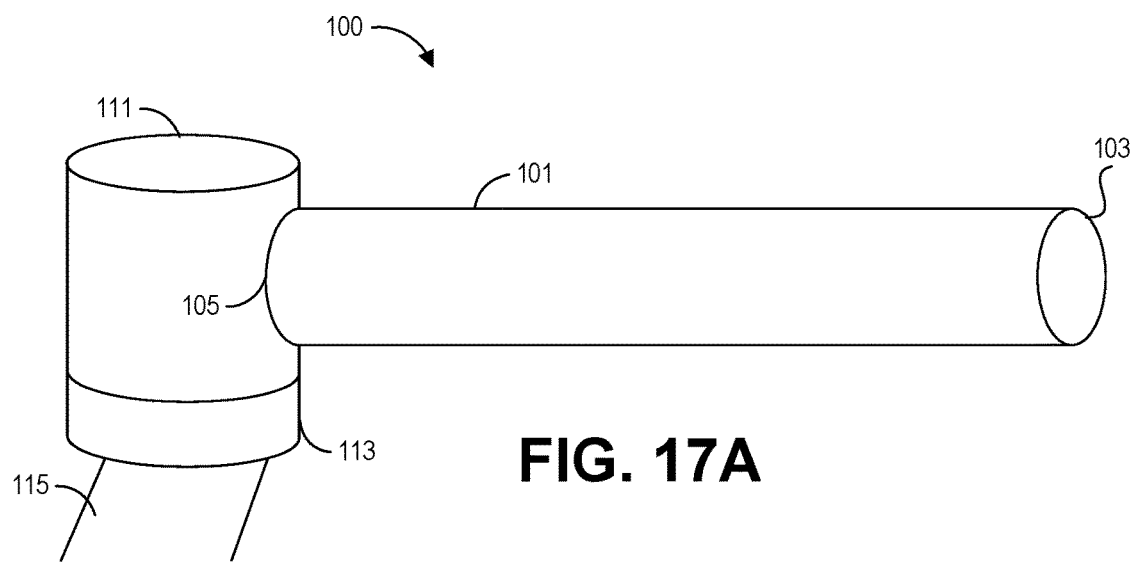
FIG. 17A illustrates the medical instrument of FIG. 16A coupled to an embodiment of an instrument positioning device.

FIG. 16A illustrates an embodiment of an elongated shaft 101 of a medical instrument 100. The elongated shaft 101 is configured for insertion, in use, into a body of a patient. In some embodiments, the elongated shaft 101 is configured for insertion, for example, via a laparoscopic procedure, into a cavity of the patient. In some embodiments, the elongated shaft 101 is configured for insertion, for example, via an endoscopic procedure, into a lumen (or luminal network) of the patient. As shown in the embodiment of FIG. 17A, the medical instrument 100 may also include an instrument base 111 (or handle) that is configured to couple the medical instrument 100 to an instrument driver 113 of an instrument positioning device 115, such as a robotic arm.

The elongated shaft 101 may be articulable (or steerable). That is, an operator may control the pose, shape, and/or articulation of the elongated shaft 101. This may allow the operator to guide or navigate the elongated shaft 101 within the patient's body. In some embodiments, the medical instrument 100 is robotically controllable as described above. A remote operator may provide control signals or inputs to an instrument positioning device that manipulates (e.g., steers, articulates, inserts, etc.) the elongated shaft 101. The elongated shaft 101 may be formed from a flexible or bendable material. In the illustrated embodiment, the elongated shaft 101 extends between a distal portion 103 and a proximal portion 105. The distal portion 103 may include a distal tip. The distal portion 103 may be the leading end of the elongated shaft 101 (i.e., the end that is inserted, in use, into the patient). The proximal end 105 may connect (either removably or permanently) to the instrument base 111 (see FIG. 17A).

The medical instrument 100 can include pull wires (or tendons) that extend through one or more sections of the elongated shaft 101. As described above, the pull wires are actuable to control the pose, shape, and/or articulation of the elongated shaft 101. In the illustrated embodiment, two pull wires 107, 109 extend through the elongated shaft 101. Although the two pull wires 107, 109 are illustrated, the medical instrument 100 may include other numbers of pull wires. For example, the medical instrument 100 can include one, two, three, four, five, six, or more pull wires. In the illustrated embodiment, the pull wires 107, 109 extend through (i.e., within) the elongated shaft 101. In another example, the pull wires 107, 109 may extend along an exterior of the elongated shaft 101. Further, although the pull wires 107, 109 are illustrated extending straight (i.e., along a linear path) through the elongated shaft 101, in other embodiments, the pull wires 107, 109 may include one or more spiraled, coiled, or helical sections.

In one example, the pull wires 107, 109 may be coupled to the distal end 103 of the elongated shaft 101. In another example (not shown), the pull wires 107, 109 may be coupled to position located proximally relative to the distal end 103 of the elongated shaft 101. At the proximal end 105, the pull wires 107, 109 can extend into the instrument base 111 (see FIG. 17A). Within the instrument base 111, the pull wires 107, 109 can be coupled to drive inputs (such as drive inputs 81 described above) that are configured actuate (i.e., tension or pull) the pull wires 107, 109. In some embodiments, each pull wire 107, 109 is coupled to an independently operable drive input. When the medical instrument 100 is coupled to the instrument driver 113 of the instrument positioning device 115, the drive inputs engage with corresponding drive outputs on the instrument positioning device 115 as described above. The drive outputs can actuate the drive inputs so as to robotically control actuation of the pull wires 107, 109.

As discussed throughout this disclosure, the elongated shaft 101 may experience compression as it is articulated or moved to various positions, poses, or shapes. The compression may be axial compression (i.e., compression measured along a longitudinal axis of the elongated shaft 101). The compression may be caused by pull wire-based movements. In other words, actuation (i.e., pulling or tensioning) the pull wires 107, 109 to control articulation, pose, and/or shape of the elongated shaft 101 may cause compression of the elongated shaft 101.

In some instances, compression of the elongated shaft 101 may be undesirable. For example, an operator may command an articulation (e.g., bending) of the elongated shaft 101. In addition to the commanded articulation, however, the elongated shaft 101 may also experience compression, resulting in an unexpected or undesired position of the distal end 103 of the elongated shaft 101. This may cause difficulties for the operator while driving (e.g., guiding or controlling) the medical instrument 100. This may also cause inaccuracy in a robotic navigation system used to drive and/or monitor the position of the medical instrument 100. For example, the robotic navigation system can use telemetry data from the instrument positioning device(s) 115 to determine or estimate a position (for example, the position of a distal tip or portion) of the medical instrument 100 within the body. Compression of the elongated body, if unaccounted for, can cause the robotic navigation system to may not accurately determine or estimate the position of the medical instrument 100. For example, if compression is not accounted for, the robotic navigation system may determine or estimate that the distal tip is more inserted into the body than it actually is.

In FIG. 16A, the elongated shaft 101 is illustrated in a default or uncompressed state. In the default state, the elongated shaft 101 has a length L measured between the distal end 103 and the proximal end 105. As will be discussed below, compression of the elongated shaft 101 may result in a decreasing the length L.

For ease of illustration and clarity, various other features of the medical instrument 100 are omitted in FIG. 16A. For example, the medical instrument 100 may also include a working channel, imaging device(s) (e.g., one or more cameras), spatial sensor(s) (e.g., position sensors, orientations sensors), etc.

Figure 16B:
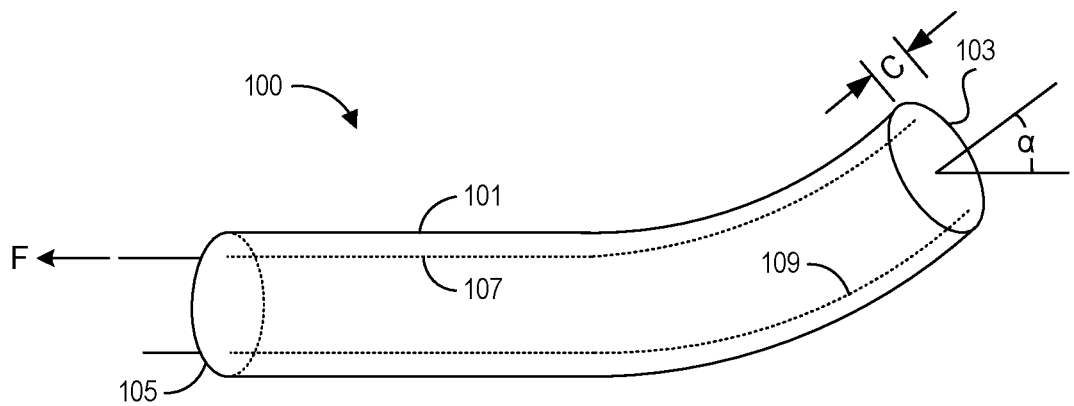
FIG. 16B depicts the elongated shaft of the medical instrument of FIG. 16A experiencing axial compression caused by an example of pull wire-based movement.

FIG. 16B depicts the elongated shaft 101 of the medical instrument 100 experiencing axial compression caused by an example of pull wire-based movement. In the illustrated example, a force F has been applied to the pull wire 107 in the illustrated direction. As illustrated, the force F causes a tension or displacement of the pull wire 107 that causes the elongated shaft 101 to articulate or bend to an angle $\alpha$, as shown. This type of pull-wire based movement may be used by an operator to steer or turn the medical instrument 100. In addition to the articulation of the elongated shaft 101 to the angle $\alpha$, the tension or displacement of the pull wire 107 also causes an axial compression of the elongated shaft 101. In the illustrated embodiment, the distal portion 103 of the elongated shaft 101 has axially compressed or retracted a distance C, as shown. That is, the length L of the elongated shaft 101 is reduced by the distance C in response to the pull wire-based movement (i.e., articulation to the angle $\alpha$) of the elongated shaft 101. As mentioned above, this may result in the distal portion 103 of the elongated shaft 101 being out of position. This axial compression may be undesirable.

Figure 16C:
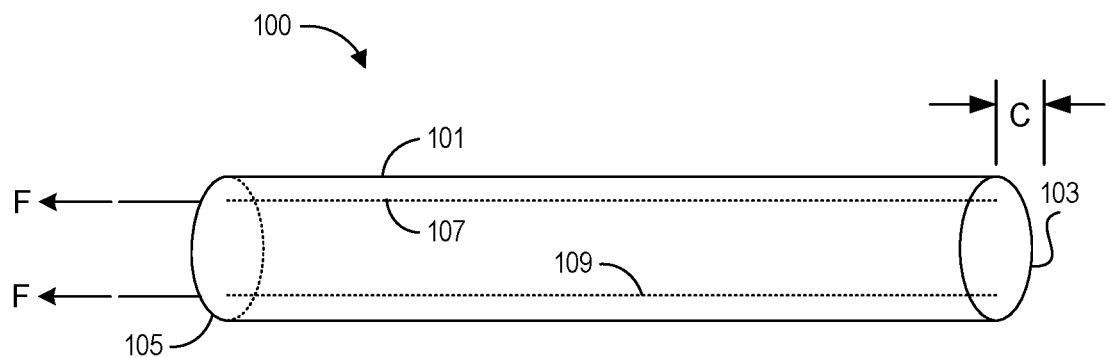
FIG. 16C depicts the elongated shaft of the medical instrument of FIG. 16A experiencing axial compression caused by another example of pull-wire based movement.

FIG. 16C depicts the elongated shaft 101 of the medical instrument 100 experiencing axial compression caused by another example of pull-wire based movement. In this example, both pull wires 107, 109 are actuated equally by the force F. Because both pull wires 107, 109 are actuated equally, the elongated shaft 101 experiences compression without bending. In the illustrated example, the length L of the elongated shaft 101 is axially compressed by a distance C as shown. This type of pull-wire based movement may be used by an operator to increase the stiffness or sensitivity of the elongated shaft 101. In some instances, however, the operator may desire to increase the stiffness or sensitivity of the elongated shaft 101 without changing the position of the distal portion 103 of the elongated shaft 101, and thus, the axial compression illustrated in FIG. 16C may be undesirable.

As described in further detail below, according to the present disclosure, axial compressions caused by pull-wire based movements (as illustrated, for example, in FIGS. 16B and 16C) can be compensated for, allowing for increased movement accuracy and an improved driving experience of medical instruments 100 including elongated shafts 101.

B. Compression Compensation

Compression of the elongated shaft 101 of the medical instrument 100 may be compensated for by moving (e.g., advancing or retracting) the medical instrument 100 with the instrument positioning device 115 (e.g., a robotic arm) to which it is coupled. For example, the extent or amount (e.g., length) of compression (e.g., along a longitudinal axis) can be calculated, determined, or estimated, and the instrument positioning device 115 can advance the medical instrument 100 a corresponding amount such that the distal portion 103 of the elongated shaft 101 remains in the expected position. In other words, the instrument positioning device 115 can advance the medical instrument 100 an amount corresponding to the amount of compression such that the distal portion 103 is located in a position that corresponds to the position of the distal portion 103 in the absence of the axial compression.

FIG. 17A illustrates the medical instrument 100 coupled to an embodiment of an instrument positioning device 115. As shown, the medical instrument 100 includes the elongated shaft 101 extending between a distal portion 103 and a proximal portion 105. The proximal portion 105 is coupled (either removably or permanently) to the instrument base 111. The instrument base 111 is coupled to the instrument driver 113 of the instrument positioning device 115. In FIG. 17A, only a portion of the instrument positioning device 115 is shown. The instrument positioning device 115 may comprise a robotic arm, such as any of the robotic arms 12, 39, 61 shown in FIGS. 1-15 described above. As mentioned above, the instrument driver 113 can include drive outputs for actuating the drive inputs in the instrument base 111 to actuate the pull wires 107, 109. The instrument positioning device 115 is movable to insert (or advance) or retract the elongated shaft 101 of the medical instrument device 100 within the patient.

Figure 17B:
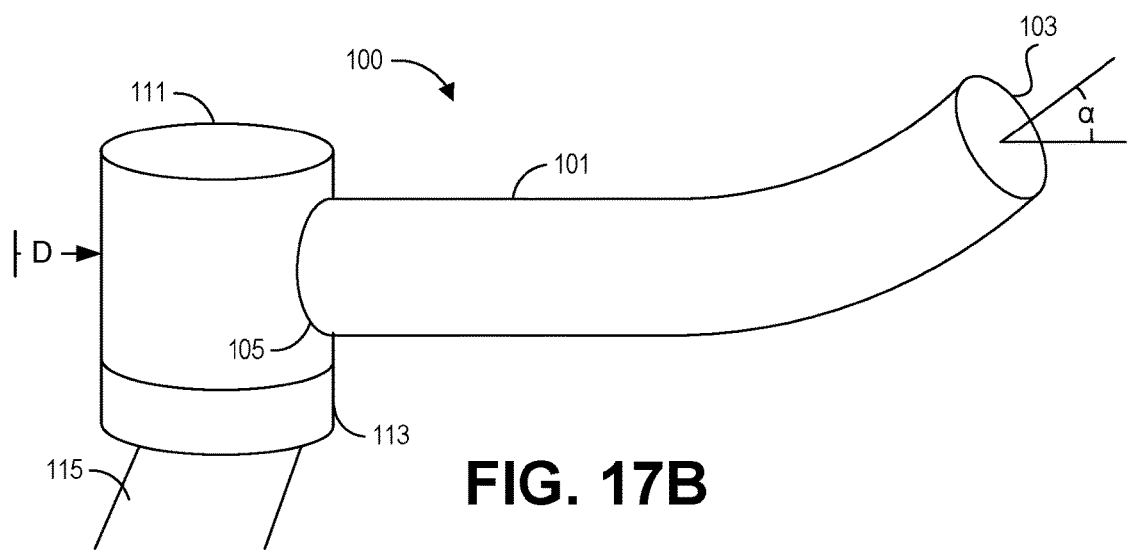
FIG. 17B depicts an example of the instrument positioning device of FIG. 17A moving to compensate for axial compression caused by pull wire-based movement of the medical instrument.

FIG. 17B depicts an example of the instrument positioning device 115 configured to move to compensate for axial compression caused by pull wire-based movement of the medical instrument 100. In FIG. 17B, the elongated shaft 101 is illustrated undergoing pull wire-based movement as shown and described in FIG. 16B, which causes a compression C of the elongated shaft 101. As shown in the example of FIG. 17B, the instrument position device 115 can move a distance D in the direction illustrated (i.e., advancing the elongated shaft 101) to compensate for the compression C. In the illustrated example, the distance D is equal to the distance of the compression C, such that the position of the distal portion 103 is advanced to the position it would have been in absent the compression. As shown, the elongated shaft 101 is articulated to the angle α and advanced the distance D to compensate for the compression C.

Figure 17C:
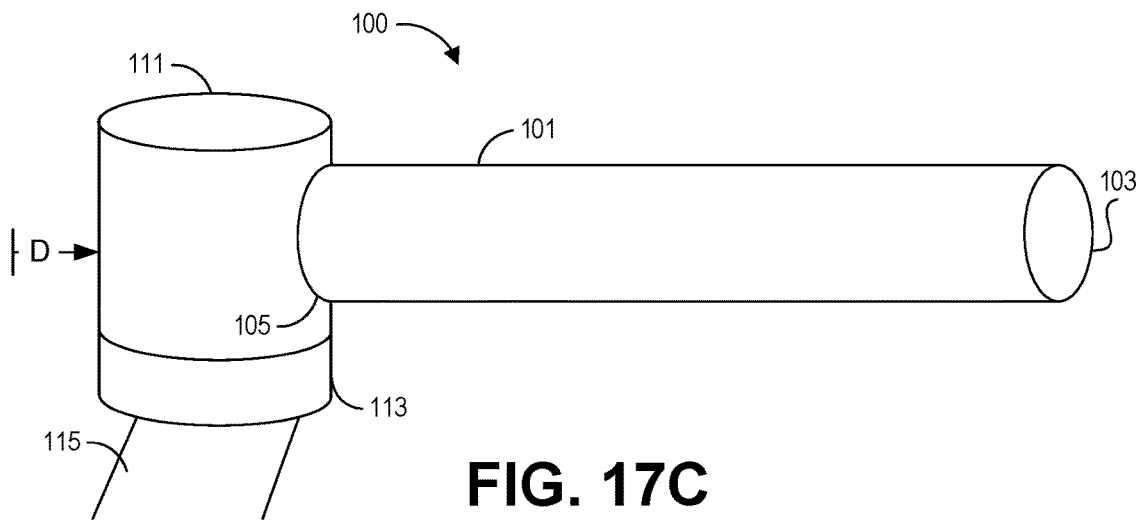
FIG. 17C depicts an example of the instrument positioning device of FIG. 17A moving to compensate for axial compression caused by pull wire-based movement of the medical instrument.

FIG. 17C depicts an example of the instrument positioning device 115 configured to move to compensate for axial compression caused by another type of pull wire-based movement of the medical instrument 100. In FIG. 17C, the elongated shaft 101 is illustrated undergoing pull wire-based movement as shown and described in FIG. 16C, which causes a compression C of the elongated shaft 101. As shown in the example of FIG. 17C, the instrument position device 115 can move a distance D in the direction illustrated (i.e., advancing the elongated shaft 101) to compensate for the compression C. In the illustrated example, the distance D is equal to the distance of the compression C, such that the position of the distal portion 103 is advanced to the position it would have been in absent the compression.

Figure 18:
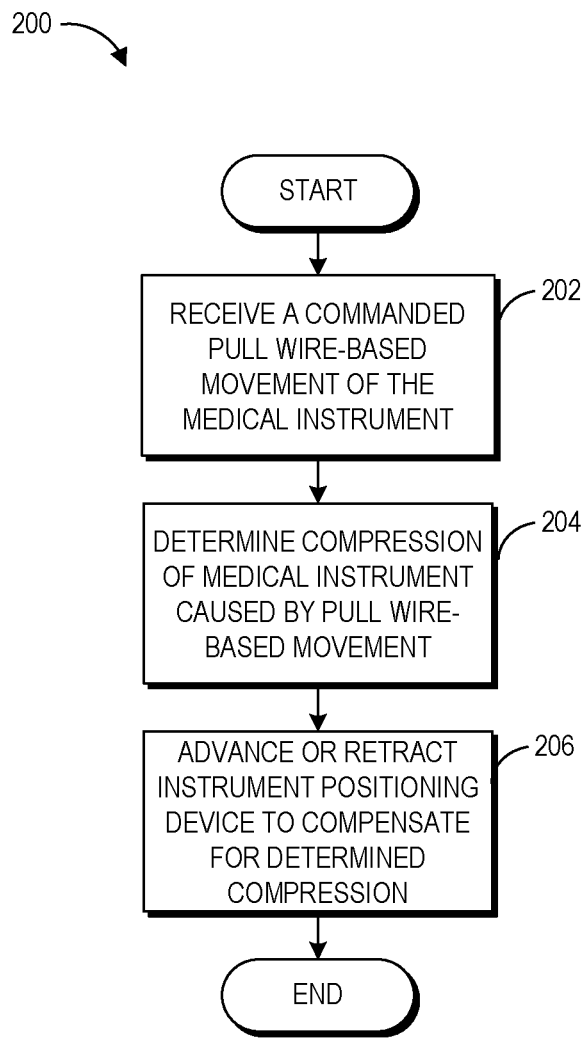
FIG. 18 is a flow chart illustrating an example method for compensating for compression in a medical instrument.

FIG. 18 is a flow chart illustrating an example method 200 for compensating for compression in a medical instrument 100. The method 200 begins at block 202 at which a commanded pull-wire based movement of the medical instrument 100 is received. The commanded pull wire-based movement may be received from an operator. The operator may provide the commanded pull-wire based movement using a remotely located input device. The commanded pull wire-based movement can be executed by the instrument positioning device 115.

Next, the method 200 moves to block 204 at which the compression of the medical instrument 100 caused by the commanded pull wire-based movement is determined. In one example, determining the compression comprises measuring the compression. In another example, determining the compression comprises calculating the compression. In another example, determining the compression comprises estimating the compression.

As will be discussed in further detail below, the compression may be determined, calculated, or estimated using one or more compression compensation parameters. The compression compensation parameter and its use are discussed in further detail below in section II.C.

In conjunction with using one or more compression compensation parameters, the compression of the medical instrument 100 can be determined, calculated, or estimated based on data from one or more other techniques. In one example, fluoroscopic images of the medical instrument 100 can be analyzed to determine compression, in addition to the use of the compression compensation parameters. In another example, the medical instrument 100 can include one or more spatial sensors (e.g., EM sensors) positioned thereon. The spatial sensors may provide position data regarding the position of the medical instrument 100. This position data can be analyzed to determine the compression of the medical instrument 100, in addition to the use of the compression compensation parameters. In another example, the medical instrument 100 can include a shape-sensing fiber. The shape-sensing fiber can provide data about the shape or pose of the medical instrument 100. This data can be analyzed to determine the compression of the medical instrument 100, in addition to the use of the compression compensation parameters. In another example, the compression of the medical instrument 100 is determined using a model, e.g., based on the shape, size, and material properties of the elongated shaft of the medical instrument 100, in addition to the use of the compression compensation parameters. In one example of determining compression of the medical instrument 100 using a model, the elongated shaft 101 of the medical instrument 100 can be divided into one or more sections that can be modeled using Euler-Bernoulli beam theory.

In another example, the compression of a first medical instrument can be measured relative to a second medical instrument, in addition to the use of the compression compensation parameters. As described below in section II.D, two or more medical instruments can be configured for telescoping use. That is, a second medical instrument can telescope within a working channel of the first medical instrument. The first medical instrument can include a spatial sensor located at its distal portion. The second medical instrument can include a spatial sensor located at its distal portion. The compression can be determined or estimated by comparing the relative position of these two position sensors. This may ensure or increase the likelihood that the distal portions of the two medical instruments remain aligned (i.e., flush).

At block 206 of the method 200, the instrument positioning device 115 that is coupled to the medical instrument 100 is moved (e.g., advanced or retracted) to compensate for the compression determined at block 204. In some instances, the instrument positioning device 115 advances the medical instrument 100 further into the patient's body to compensate for the determined compression. In one example, the distance advanced into the patient body is approximately equal to the determined compression. In another example, the distance advanced is less than the determined compression. In another example, the distance advanced is greater than the determined compression. As described below in section II.D, in embodiments that include telescoping medical instruments, one medical instrument can be retracted to compensate for the compression, the other medical instrument can be advanced to compensate for the compression, or one medical instrument can be advanced and the other medical instrument can be retracted to compensate for the compression.

In some embodiments, block 206 is performed substantially at the same time as the pull wire-based movement is executed. That is, the instrument positioning device 115 advances or retracts to compensate for the compression at substantially the same time as the pull wires are actuated to perform the pull wire-based movement. In some embodiments, this maintains or helps to maintain the correct or desired positioning of the distal portion 103 of the elongated shaft 101 throughout the commanded pull wire-based movement.

In some embodiments, the blocks 202, 204, 206 of the method 200 can be performed in a loop to provide compression compensation for each newly commanded pull wire-based movement of the medical instrument.

The method 200 can include other blocks or steps in addition to those illustrated. In some embodiments, not all illustrated blocks of the method 200 need be implemented.

C. Compression Compensation Parameter

The compression of the elongated shaft 101 can be determined, calculated, or estimated using one or more compression compensation parameters. The compression compensation parameter may be determined during a calibration of the medical instrument 100. Example calibration methods and processes, during which the compression compensation parameter can be determined, are described below in section II.F.

The compression compensation parameter can be specific to a particular or specific medical instrument 100. That is, for a specific medical instrument 100, the compression compensation parameter can be determined during calibration of that particular medical instrument 100. In this way, the compression compensation parameter can account for the unique properties (caused by, for example, material variation, manufacturing process variation, etc.) of that particular medical instrument 100. The compression compensation parameter can be associated with the particular medical instrument 100. For example, the compression compensation parameter can be stored in a memory or non-transitory computer readable medium of the medical instrument 100. In some embodiments, the compression compensation parameter is stored in a remote database and associated with the particular medical instrument 100 such that it can be accessed and used to determine compression when the particular medical instrument 100 is used.

In another example, the compression compensation parameter can be specific to a class, batch, or model of similar medical instruments 100. That is, the same compression compensation parameter can be used for a class, batch, or model of similar medical instruments 100. In some embodiments, a single or several medical instruments 100 are calibrated to determine a compression compensation parameter that will be used by a larger group of similar medical instruments 100.

In some embodiments, the compression compensation parameter is determined using a model that, for example, takes into account, for example, the material properties and dimensions of the medical instrument 100. In one example, the elongated shaft 101 of the medical instrument 100 can be divided into one or more sections that can be modeled using Euler-Bernoulli beam theory.

The compression compensation parameter can be a value, factor, or parameter that relates a characteristic of the pull wire-based movement to axial compression. As one example, the compression compensation parameter can relate an angle of articulation of the elongated shaft 101 of the medical instrument 100 to axial compression. For example, the compression compensation parameter can relate x degrees of articulation of the elongated shaft 101 to y millimeters of axial compression. The compression compensation parameter can relate a commanded angle of articulation to axial compression. In another example, the compression compensation parameter can relate a measured angle of articulation to axial compression. In some instances, the angle of articulation is measured using spatial sensors (such as EM sensors), shape-sensing fiber, medical imaging (e.g., fluoroscopy), or other methods.

In another example, the compression compensation parameter can relate tension in a pull wire to axial compression of the elongated shaft 101. The medical instrument 100 may include one or more tension sensors for measuring the tension in the pull wires.

In another example, the compression compensation parameter can relate displacement (e.g., linear displacement) of a pull wire to axial compression of the elongated shaft 101. The medical instrument 100 may include a linear actuator for actuating the pull wire. The compression compensation parameter can relate linear movement of the actuator or the pull wire to axial compression of the elongated shaft 101. For example, the compression compensation parameter can relate x millimeters of linear displacement of the pull wire or actuator to y millimeters of axial compression.

In some embodiments, the medical instrument 100 comprises rotational actuators that actuate the pull wires. For example, the pull wires may be mounted on pulleys which are rotated to actuate the pull wires. The compression compensation parameter can relate rotation of a pulley around which the pull wires are wound to axial compression of the elongated shaft. For example, the compression compensation parameter can relate x degrees of rotation of the pulley to y millimeters of axial compression.

In the above-cited examples, the compression compensation parameter is a parameter that linearly relates a characteristic of pull wire-based movement to axial compression. This need not be the case in all embodiments. For example, in some embodiments, the compression compensation parameter can comprise a function that relates the characteristic of pull wire-based movement to axial compression, wherein the function is non-linear.

In some embodiments, only a single compression compensation parameter is associated with the medical instrument 100. In some embodiments, multiple compression compensation parameters are associated with the medical instrument 100. For example, different compression compensation parameters can be associated with each of the different pull wires. As another example, different compression compensation parameters can be used to compensate for pull wire-based movements in different directions. As another example, multiple compression compensation parameters could be used to model non-linear compression of the elongated body 101, using, for example polynomial, exponential, or other non-linear functions. In some instances, the number of compression parameters and/or the type of function (linear or non-linear) can be varied to closely model the relationship of compression to the input.

As described above, the compression compensation parameter can be used to relate one or more characteristics of pull wire-based movement to axial compression. Thus, the compression compensation parameter can be used to determine, calculate, or estimate axial compression of the elongated shaft 101 for a given pull wire-based movement. In some embodiments, the compression compensation value is used at block 204 of the method 200 described above.

D. Compression Compensation in Telescoping Medical Instruments

Although the descriptions above have focused primarily on a single medical instruments, the compression compensation methods and systems described herein can be applied in systems that include telescoping medical instruments, such as, for example, systems that include a second medical instrument that telescopes within a working channel of a first medical instrument. The systems and methods may also be applied in systems that include more than two (e.g., three, four, five, or more) telescoping medical instruments.

FIG. 19A illustrates an embodiment of a second medical instrument 120 telescoping within a working channel 117 of a first medical instrument 100. In the illustrated embodiment, the first medical instrument 100 is configured as previously described, including an elongated shaft 101 and an instrument base 111. The elongated shaft 101 includes a working channel 117 extending therethrough. The first medical instrument 100 is coupled to a first instrument driver 113 of a first instrument positioning device 115. The first instrument positioning device 115 is configured to move to advance or retract the first medical instrument 100.

The second medical instrument 120 is configured similar to the first medical instrument 100, including an elongated shaft 121 extending between a distal portion 123 and a proximal portion 125. The proximal portion 125 is connected (either removably or permanently) to a second instrument base 131. The second instrument base 131 is coupled to a second instrument driver 133 of a second instrument positioning device 135. The second instrument positioning device 135 is configured to move to advance or retract the second medical instrument 120.

As shown, the elongated shaft 121 of the second medical instrument 120 extends through the working channel 117 of the first medical instrument 100. The second instrument positioning device 135 is configured to move to advance or retract the second medical instrument 120 through the working channel 117 of the first medical instrument 100.

Although not illustrated, in some examples, the second medical instrument 120 may also include a working channel for receiving a third medical instrument.

In the configuration illustrated in FIG. 19A, the distal portion 123 of the second medical instrument 120 is aligned with the distal portion 103 of the first medical instrument 100. In some instances, this may be a preferred configuration for driving the medical instruments 100, 120. For example, the first and second medical instruments 100, 120 can be in this configuration (with distal portions 103, 123 aligned or flush) as they are navigated through the body to a target site.

The first medical instrument 100 can include pull wires for controlling the articulation, shape, and/or pose of the first elongated shaft 101. The second medical instrument 120 can include pull wires for controlling the articulation, shape, and/or pose of the second elongated shaft 121. In other examples, the first medical instrument 100 can be a passive instrument that does not include pull wires (i.e., a non-steerable instrument) or the second medical instrument 120 can be a passive instrument that does not include pull wires (i.e., a non-steerable instrument).

FIG. 19B depicts an example of axial compression of the first and second medical instruments 100, 120 caused by pull wire-based movement. In the illustrated example, the first and second medical instruments 100, 120 are articulated from the position shown in FIG. 19A to an angle shown in FIG. 19B. Either or both the first and second medical instruments 100, 120 can experience compression. In the position illustrated in FIG. 19B, the second elongated shaft 121 extends outwardly from the distal end 103 of the first elongated shaft 101. This may be caused by the axial compression of the first and/or second elongated shafts 101, 121. This may be undesirable. For example, as noted above, it is often desirable to drive the first and second medical instruments 100, 120 with the distal ends 103, 123 positioned flush.

Figure 19C:
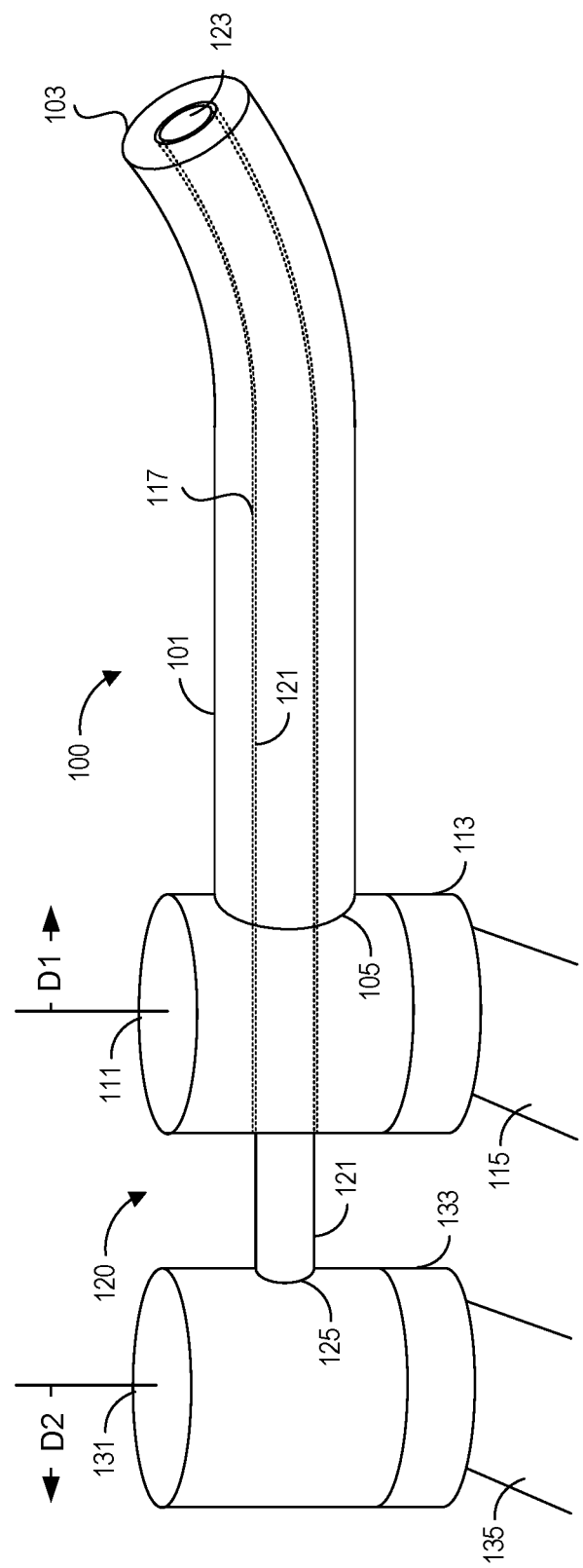
FIG. 19C illustrates that the axial compression of FIG. 19B can be compensated for by moving first and/or second instrument positioning devices coupled to the first and second medical instruments, respectively.

FIG. 19C illustrates that the axial compression illustrated in FIG. 19B can be compensated for by moving the first and/or the second instrument positioning devices 115, 135 to compensate. To compensate for axial compression, and return the distal portions 103, 123 to a flush position, the system can either move the first instrument positioning device 115 a distance D1 in the direction indicated to advance the first medical instrument 100, move the move the second instrument positioning device 115 the distance D2 in the direction indicated to retract the second medical instrument 120, or perform a combined movement of the first and second instrument positioning devices 115, 135 to both advance the first medical instrument 100 and retract the second medical instrument 120.

In one example, a "compression compensation ratio" (CCR) can be defined or set for each medical instrument 100, 120. The CCR can be a value between zero and one. The CCR is one when the compressed medical instrument compensates fully for its own compression and zero when the reciprocal medical instrument (which may be uncompressed or may also be articulated and compressed) is moved to fully compensate for compression of the compressed medical instrument. Using the CCR for each medical instrument it is possible to define equations for defining the movement or insertion of the first and second medical instruments 100, 120, as follows:

$$\text{insertion}_{2nd} = (1 - CCR_{1st}) \cdot \text{compression}_{1st} - CCR_{2nd} \cdot \text{compression}_{2nd}$$

$$\text{insertion}_{1st} = (1 - CCR_{2nd}) \cdot \text{compression}_{2nd} - CCR_{1st} \cdot \text{compression}_{1st}$$

Using the principals and equations described above, as well as CCRs for each medical instrument 100, 120, it is possible to compensate for compression of the first and/or second medical instrument 100, 120 by moving only the first medical instrument 100, by moving only the second medical instrument 120, or by moving both medical instruments 100, 120.

In some embodiments, retractions (CCR=0) of the first and second medical instruments 100, 120 are preferred. For example, in some instances, retractions of the first and second medical devices 100, 120 may be safer than insertions of the medical instruments. In some embodiments, however, insertions (CCR=1) are possible. Additionally, CCRs between zero and one can also be used.

Additionally, the CCR values can influence the spatial path taken by the distal portion 103, 123 of the first and second medical devices 100, 120. For example, a CCR of one may correspond to a more spherical path, while a CCR of zero may create a more obtuse path (along an ellipsoid instead of a sphere). In some embodiments, the CCR value can be adjusted so that an optimal path can be tuned empirically. In some instances, the CCR value is adjusted during device calibration to deliver a target motion path of the distal tip of the elongated body 101. During calibration, adjustment can be performed either manually or automatically through analysis of tip path.

E. Example Medical Instruments and Systems for Compression Compensation

Figure 20:
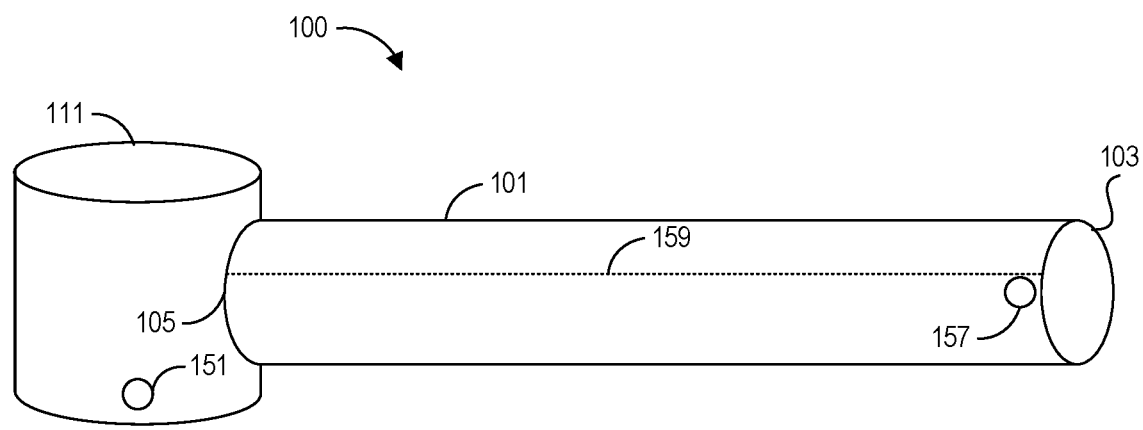
FIG. 20 illustrates an embodiment of a medical instrument configured to compensate for axial compression.

FIG. 20 illustrates an embodiment of a medical instrument 100 configured to compensate for axial compression. In the illustrated embodiment, the medical instrument 100 is configured as described above, including, for example, an elongated shaft 101 extending between a distal portion 103 and a proximal portion 105. The elongated shaft 101 may include one or more pull wires for articulating the elongated shaft. The elongated shaft 101 is connected to an instrument base 111. The instrument device 111 is configured to couple to an instrument driver 113 of an instrument positioning device 115. The instrument positioning device 115 can be configured to move the medical instrument 100 to advance or retract the elongated shaft 101 within a patient.

As illustrated, for some embodiments, the medical instrument 100 includes a computer readable medium 151. The computer readable medium 151 can be positioned on or within the instrument base 111. In another example, the computer readable medium 151 can be positioned on or within the elongated shaft 101.

The computer readable medium 151 can store information associated with the medical instrument 100. For example, the computer readable medium 151 can store one or more compression calibration parameters as discussed above in section II.C.

The computer readable medium 151 can include a computer readable code which can be read by another device. For example, the computer readable code can be a radio frequency identifier (RFID) tag. Data stored in the computer readable medium 151, such as the compression compensation parameter, can be accessed by another device by scanning the RFID tag with an RFID reader. Other types of computer readable codes may also be used, such as bar codes, QR codes, etc.

The medical instrument 100 can include communication circuitry for communicating data stored in the computer readable medium 151 to other devices. Such communication circuitry may be wired or wireless.

The medical instrument 100 can include one or more EM sensors 157. The EM sensors 157 are positioned on or within the elongated shaft 101. As illustrated, an EM sensor 157 is positioned at the distal portion 103 of the elongated shaft 101. The EM sensors 157 may be configured to provide position and/or orientation data about the medical instrument 100. The EM sensors 157 provide position and/or orientation data relative to an externally generated EM field. Other types of spatial sensors can also be included.

The medical instrument 100 can include a shape-sensing fiber 159. The shape-sensing fiber 159 may extend along or within the elongated shaft 159. The shape-sensing fiber 159 can provide data related to the shape, articulation, or pose of the medical instrument 100.

The medical instrument 100 can include one or more tension sensors associated with the one or more pull wires. The tension sensors can be configured to provide tension data for the one or more pull wires. In some embodiments, the tensions sensors are positioned in the instrument base 111.

Figure 21:
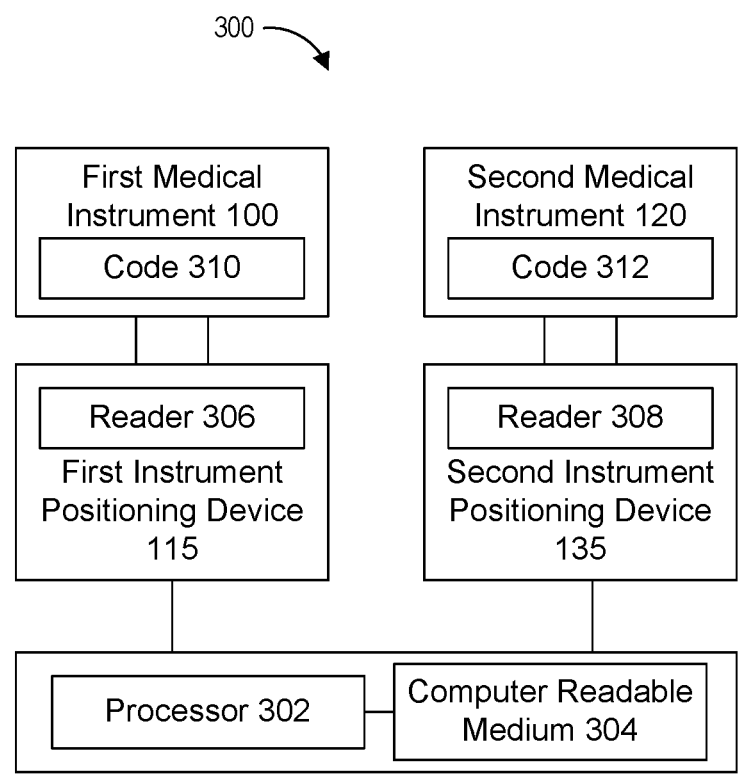
FIG. 21 depicts a block diagram of an embodiment of a system configured to compensate for axial compression of medical instruments.

FIG. 21 is a block diagram depicting a system 300 configured to compensate for compression of medical instruments 100, 120. In the illustrated embodiment, the system 300 includes a processor 302 (or a plurality of processors) connected to a memory or computer readable medium 304 (or a plurality of computer readable media). The computer readable medium 304 can include instructions that can be executed by the processor 302 to control the system 300.

In the illustrated embodiment, the system 300 includes a first instrument positioning device 115 coupled to a first medical instrument 100. The first medical instrument 100 includes a computer readable code 310. The first instrument positioning device 115 includes a code reader 306. The code reader 306 is configured to read the computer readable code 310 on the first medical instrument 100. In some embodiments, the computer readable code 310 is an RFID tag and the reader 306 is a RFID reader. The computer readable code 310 can store data related to the first medical instrument 100, such as compression compensation parameters. The code reader 306 can read the data from the machine readable code 310. In some embodiments, the data read from the computer readable code 310 can be communicated to the processor 302 for use in controlling the system 300.

The system 300 may also include additional instrument positioning devices coupled to additional medical instruments. For example, as illustrated, the system 300 includes a second instrument positioning device 135 coupled to a second medical instrument 120. The second instrument positioning device 135 includes a reader 308 configured to read a machine readable code 312 on the second medical instrument 120 in the manner previously described.

In some embodiments, the system 300 compensates for compression in the first and second medical instruments using the method 200 described above.

In some embodiments, the second medical instrument 120 telescopes within a working channel of the first medical instrument 100. The system 300 may use the CCRs described above to compensate for compression as described in section II.D.

The computer readable medium 304 can include instructions that configure the processor 302 to cause the system 300 to determine, based at least in part on information indicative of a pull wire-based movement of an elongated shaft 101 of a first medical instrument 100 and a compression compensation parameter, an axial compression of the elongated shaft 101 of the first instrument 100. The compression compensation parameter can be read, using the reader 306, from the computer readable code 310. The instructions can further be configured to move the first instrument positioning device 115 connected to the first medical instrument 100 to compensate for the axial compression of the first elongated shaft.

F. Example Calibration Processes

The compression compensation parameter can be determined during a calibration process of the medical instrument 100. The calibration process can include articulating the medical instrument to a first position with a pull wire-based movement, determining the compression of the medical instrument, and relating a characteristic of the pull wire-based movement to the determined compression to determine the compression compensation parameter.

The calibration process can include articulating the medical instrument 100 to a variety of different positions and determining compression and compression compensation parameters for each. In some embodiments, a single compression compensation parameter is derived from the variety of different articulated positions.

The calibration process can include attaching one or more spatial caps to the medical instrument 100. The one or more spatial caps can be calibrated to provide valid metrology or measurement of the pose (e.g., position and/or orientation) of the medical instrument 100. In some instances, the one or more spatial caps are calibrated to provide metrology or measurement or pose of the distal tip of the elongated body 101 of the medical instrument 100. The spatial caps can include spatial sensors, such as EM sensors, that provide position and/or orientation data about the articulation, pose, or position of the medical instrument 100. The spatial caps can be used to measure the articulation and/or compression of the medical instrument 100. The one or more spatial caps can be used to further validate the spatial sensors included on the medical instrument 100.

In other embodiments, feedback from an imaging device included on the medical instrument 100 (for example, at a distal tip of the elongated body) can be analyzed using an external tracking device to estimate tip pose instead of or in addition to the use of the one or more spatial caps. Triangulation, projection or direct or manual measurement (e.g., using a protractor) methods can also be used in addition to or in place of the one or more spatial caps.

The articulation and/or compression of the medical instrument 100 can be determined from spatial sensors positioned on the medical instrument 100 itself. For example, the articulation and/or compression can be determined using EM sensors or shape-sensing fiber as previously described.

Figure 22:
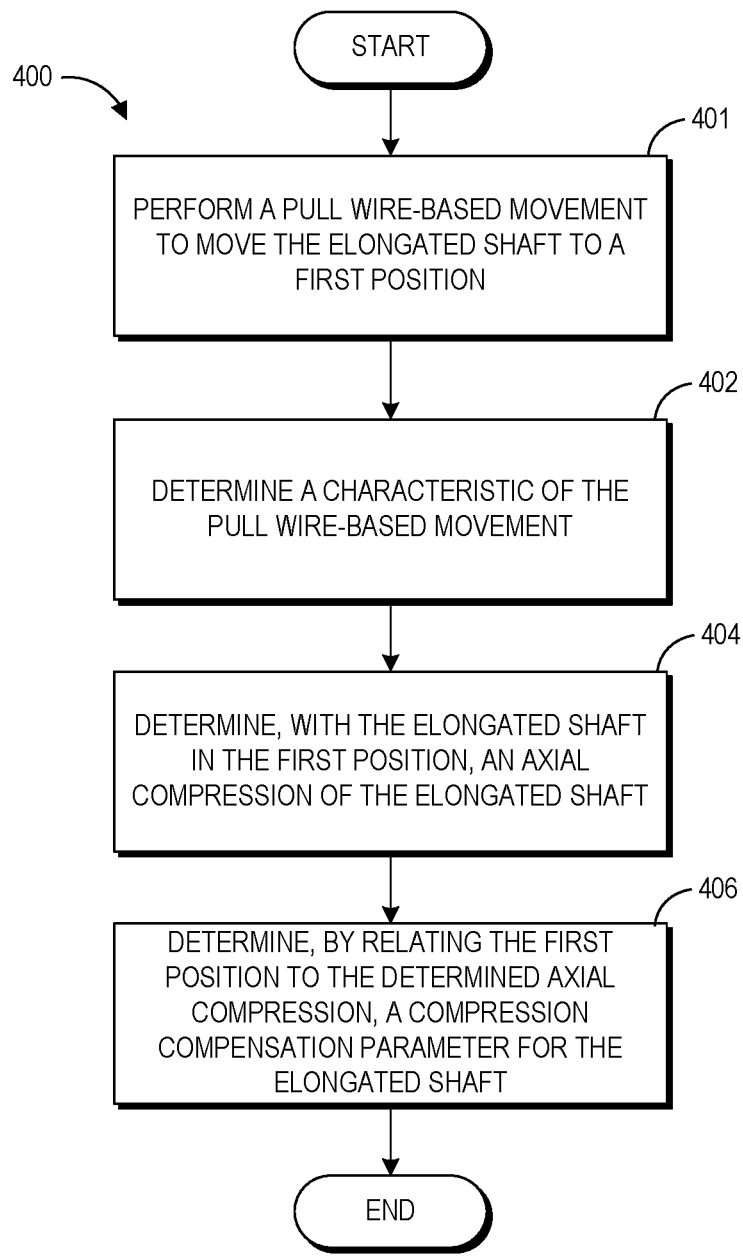
FIG. 22 is a flow chart illustrating an example method for calibrating a medical instrument.

FIG. 22 is a flow chart illustrating an example method 400 for calibrating a medical instrument 100. The method 400 begins at block 401, where a pull wire-based movement is performed to move the elongated shaft 101 to a first position. In some instances, articulating the elongated shaft 101 comprises tensioning, pulling, or otherwise actuating a pull wire connected to a distal portion 103 of the elongated shaft 101.

The method 400 continues at block 402, where a characteristic of the pull wire-based movement is determined. In some instances, determining the characteristic of the pull wire-based movement can include pull wire tension, pull wire displacement, actuator displacement, commanded angle of articulation, measured angle of articulation, etc.

In some examples, the method 400 further includes attaching one or more spatial caps to the distal portion 103 of the elongated shaft 101. The one or more spatial caps can be configured to provide spatial data about the location and orientation of the distal portion 103 of the elongated shaft 101. In some embodiments, determining the pull wire-based movement comprises analyzing the spatial data from the spatial cap. In some embodiments, the one or more spatial caps include one or more EM sensors. In some embodiments, determining the pull wire-based movement comprises measuring an angle of the elongated shaft.

At block 404, with the elongated shaft 101 in the first position, the compression of the elongated shaft 101 is determined. In an example, determining the compression can include analyzing the spatial data from the spatial cap. In another example, the elongated shaft 101 comprises a spatial sensor configured to provide spatial data about the location and orientation of the distal portion 103 of the elongated shaft 101, and determining the pull wire-based movement includes analyzing the spatial data from the spatial sensor. In another example, determining the axial compression comprises measuring a length of the elongated shaft.

At block 406, a compression compensation parameter is determined by relating the first position to the determined compression of the elongated shaft 101. In some embodiments, the method 400 further includes storing the compression compensation parameter in a non-transitory computer readable medium of the first medical instrument 100.

3. Implementing Systems and Terminology

Implementations disclosed herein provide systems, methods and apparatus for compensating for compression in elongated shafts of medical instruments. Compression can be determined, in some instances, using a compression compensation parameter determined during calibration of the medical instrument, and compensated for by moving the medical instrument with an instrument positioning device coupled thereto.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic system, comprising:
    a robotic arm comprising:
        a series of linkages connected by a series of joints; and
        an instrument driver coupled to a distal end of the series of linkages; and
    a medical instrument, comprising:
        an elongated shaft extending between a distal portion and a proximal portion, the elongated shaft configured for insertion, in use, into a lumen of a patient;
        an instrument base connected to the proximal portion of the elongated shaft, the instrument base including an attachment interface configured to facilitate attachment to the robotic arm;
        a non-transitory computer readable medium storing a compression compensation parameter that relates movement of the elongated shaft to axial compression of the elongated shaft; and
        a pull wire connected to the distal portion of the elongated shaft, the pull wire extending along the elongated shaft between the distal portion and a drive input positioned at the instrument base, the drive input configured to actuate the pull wire to cause movement of the elongated shaft;
    wherein the robotic arm is configured to move the instrument driver along a virtual rail to advance or retract the instrument base based at least in part on the stored compression compensation parameter, and wherein the robotic arm moves to advance or retract the instrument base at substantially the same time as the drive input actuates the pull wire to cause movement of the elongated shaft.

2. The robotic system of claim 1, wherein movement of the elongated shaft comprises articulation of the elongated shaft, and wherein the compression compensation parameter relates an angle of articulation of the elongated shaft to an axial length of compression of the elongated shaft.

3. The robotic system of claim 2, wherein the angle of articulation comprises a commanded angle of articulation.

4. The robotic system of claim 2, wherein the angle of articulation comprises a measured angle of articulation.

5. The robotic system of claim 4, further comprising at least one electromagnetic (EM) sensor positioned on the elongated shaft, wherein the measured angle of articulation is determined based on a signal from the EM sensor.

6. The robotic system of claim 1, wherein the compression compensation parameter relates a pull wire displacement to an axial length of compression of the elongated shaft.

7. The robotic system of claim 1, wherein the drive input comprises a linear drive input, and wherein the compression compensation parameter relates a linear displacement of a portion of the linear drive input to an axial length of compression of the elongated shaft.

8. The robotic system of claim 1, wherein the non-transitory computer readable medium comprises a radio frequency identification (RFID) tag.

9. The robotic system of claim 8, wherein the RFID tag is positioned at the instrument base.

10. The robotic system of claim 9, wherein the RFID tag is configured to communicate the compression compensation parameter when activated by a RFID reader of the robotic arm.

11. The robotic system of claim 1, wherein the elongated shaft comprises a sheath having a channel formed therethrough, the channel extending along an axis of the sheath.

12. The robotic system of claim 1, further comprising one or more additional pull wires.

13. The robotic system of claim 1, wherein the non-transitory computer readable medium is remotely located from the instrument base and the elongated shaft.

14. The robotic system of claim 1, wherein the non-transitory computer readable medium is positioned on or within the elongated shaft.

15. The robotic system of claim 1, wherein the compression compensation parameter is a non-linear function.

16. The robotic system of claim 1, wherein the compression compensation parameter is used to calculate axial compression of the elongated shaft for a given movement measurement of the pull wire.

17. A robotic system, comprising:
    a robotic arm; and
    a medical instrument, comprising:
        an elongated shaft extending between a distal portion and a proximal portion;
        an instrument base connected to the proximal portion of the elongated shaft, the instrument base including a drive input configured to be driven by a corresponding drive output of the robotic arm;
        a non-transitory computer readable medium storing a compression compensation parameter that relates movement of the elongated shaft to axial compression of the elongated shaft; and
        a pull wire connected to the distal portion of the elongated shaft and the drive input;
    wherein the robotic arm is configured to move along a virtual rail to advance or retract the instrument base based at least in part on the stored compression compensation parameter, and wherein the robotic arm moves to advance or retract the instrument base at substantially the same time as the drive input actuates the pull wire to cause movement of the elongated shaft.

18. The robotic system of claim 17, wherein movement of the elongated shaft comprises articulation of the elongated shaft, and wherein the compression compensation parameter relates an angle of articulation of the elongated shaft to an axial length of compression of the elongated shaft.

19. The robotic system of claim 18, wherein the angle of articulation comprises one of a commanded angle of articulation and a measured angle of articulation.

20. The robotic system of claim 17, wherein the compression compensation parameter relates a pull wire displacement to an axial length of compression of the elongated shaft.

21. The robotic system of claim 17, wherein the non-transitory computer readable medium comprises a radio frequency identification (RFID) tag.

22. The robotic system of claim 21, wherein the RFID tag is positioned at the instrument base.

23. The robotic system of claim 22, wherein the RFID tag is configured to communicate the compression compensation parameter when activated by a RFID reader of the robotic arm.

24. The robotic system of claim 17, wherein the elongated shaft comprises a sheath having a channel formed therethrough, the channel extending along an axis of the sheath.

25. A medical instrument, comprising:
an elongated shaft extending between a distal portion and a proximal portion, the elongated shaft configured for insertion, in use, into a lumen of a patient;
an instrument base connected to the proximal portion of the elongated shaft, the instrument base including an attachment interface configured to facilitate attachment to a robotic arm;
a linear drive input positioned at the instrument base;
a non-transitory computer readable medium storing a compression compensation parameter that relates a linear displacement of a portion of the linear drive input to an axial length of compression of the elongated shaft; and
a pull wire connected to the distal portion of the elongated shaft, the pull wire extending along the elongated shaft between the distal portion and the linear drive input, the linear drive input configured to actuate the pull wire to cause movement of the elongated shaft based at least in part on the stored compression compensation parameter.

26. The medical instrument of claim 25, wherein movement of the elongated shaft comprises articulation of the elongated shaft, and wherein the compression compensation parameter relates an angle of articulation of the elongated shaft to an axial length of compression of the elongated shaft.

27. The medical instrument of claim 25, wherein the compression compensation parameter relates a pull wire displacement to an axial length of compression of the elongated shaft.

* * * * *